(12) United States Patent
Jones et al.

(10) Patent No.: US 12,150,865 B2
(45) Date of Patent: Nov. 26, 2024

(54) IMPLANT PACKAGING CARTRIDGE AND INSERTION TOOL

(71) Applicant: GLOBUS MEDICAL, INC., Audubon, PA (US)

(72) Inventors: Meaghan Jones, Philadelphia, PA (US); Jody L. Seifert, Birdsboro, PA (US); Jason Gray, East Greenville, PA (US); Prem Ramakrishnan, Trappe, PA (US)

(73) Assignee: Globus Medical, Inc., Audubon, PA (US)

( * ) Notice: Subject to any disclaimer, the term of this patent is extended or adjusted under 35 U.S.C. 154(b) by 603 days.

(21) Appl. No.: 17/405,412

(22) Filed: Aug. 18, 2021

(65) Prior Publication Data

US 2022/0023069 A1 Jan. 27, 2022

(51) Int. Cl.
| | | |
|---|---|---|
| A61F 2/44 | (2006.01) | |
| A61B 17/17 | (2006.01) | |
| A61F 2/46 | (2006.01) | |
| A61F 2/30 | (2006.01) | |

(52) U.S. Cl.
CPC ........ *A61F 2/4611* (2013.01); *A61B 17/1728* (2013.01); *A61B 17/1757* (2013.01); *A61F 2/4425* (2013.01); *A61F 2/4455* (2013.01); *A61F 2002/30594* (2013.01); *A61F 2002/3082* (2013.01); *A61F 2002/30884* (2013.01); *A61F 2002/4629* (2013.01)

(58) Field of Classification Search
CPC .......................... A61F 2/0095; A61F 2/4611
See application file for complete search history.

(56) References Cited

U.S. PATENT DOCUMENTS

| | | | |
|---|---|---|---|
| 5,667,513 A | 9/1997 | Torrie et al. | |
| 7,300,441 B2* | 11/2007 | Haid | A61B 17/142 |
| | | | 606/90 |
| 8,328,851 B2* | 12/2012 | Curran | A61F 2/4425 |
| | | | 606/279 |
| 8,579,911 B2* | 11/2013 | Dudasik | A61F 2/4657 |
| | | | 606/86 A |
| 9,526,634 B2* | 12/2016 | Errico | A61F 2/0095 |
| 9,603,716 B2* | 3/2017 | Zubok | A61F 2/4611 |
| 2004/0059318 A1* | 3/2004 | Zhang | A61F 2/4611 |
| | | | 606/1 |
| 2005/0033305 A1* | 2/2005 | Schultz | A61F 2/4425 |
| | | | 606/99 |
| 2006/0030860 A1* | 2/2006 | Peterman | A61F 2/4611 |
| | | | 606/99 |
| 2006/0111784 A1* | 5/2006 | Grinberg | A61F 2/4611 |
| | | | 623/23.39 |
| 2007/0168040 A1* | 7/2007 | Raymond | A61F 2/4611 |
| | | | 623/17.15 |
| 2008/0133016 A1 | 6/2008 | Heinz | |
| 2008/0287957 A1 | 11/2008 | Hester et al. | |

(Continued)

*Primary Examiner* — Nicholas W Woodall

(57) ABSTRACT

A packaging insert/cartridge for use with an implant having first and second components is provided. The packaging insert includes a main body, a snap fit latch extending proximally from the main body and a spacer extending distally from the main body and configured to be disposed between the first and second components of the implant. The snap fit latch is adapted to snap fit over a mating part of an implant inserter.

14 Claims, 26 Drawing Sheets

(56) References Cited

U.S. PATENT DOCUMENTS

2009/0012529 A1\* 1/2009 Blain .................. A61B 17/808
                                                606/86 A
2010/0100138 A1   4/2010 Reynolds et al.
2014/0249636 A1\* 9/2014 Bouchot ................ A61F 2/442
                                                623/17.16

\* cited by examiner

IMPLANT PACKAGING CARTRIDGE AND INSERTION TOOL

CROSS REFERENCE TO RELATED APPLICATIONS

FIELD OF THE INVENTION

The present disclosure generally relates to treatment of spinal irregularities. In particular, in one or more embodiments, the present disclosure relates to insertion tool assemblies that can be used to position an implant at a target location in a patient.

BACKGROUND

Medical devices may be implanted in patients in a variety of different surgical procedures. In the treatment of spinal irregularities, for example, implants may be inserted within a space created by complete or partial removal of an intervertebral disc between adjacent vertebrae. One example of an implant that may be placed into the disc space of a patient's spine is a spacer that can maintain height of the spine and/or restore stability to the spine. Another example of an implant that can be placed into a patient's spine is an artificial disc that can replace the disc while maintaining vertebral height and also preserving mobility in the treated vertebral segment.

A spinal implant can be inserted into the patient using an anterior, lateral, or posterior approach. Combinations of these approaches (e.g., posterolateral) can also be used. In each of these approaches, the surgeon typically has little room to maneuver the implant to the desired location. In addition, while maneuvering the implant, the surgeon should use care to avoid organs, nerves, and other structures that could result in damage to the patient. Accordingly, insertion tool assemblies that can be used to position the implant in the patient should securely hold the implant without allowing articulation, e.g., flexion/extension, lateral bending or axial rotation. Further, the connection between the implant and the insertion tool assembly should be rigid enough for impaction when being used by the surgeon. In addition, the implant should be readily removed from the insertion tool assembly once it has been placed in the desired location within the patient.

Several different insertion tool assemblies have been used heretofore to position implants in a patient. For instance, one type of insertion tool assembly that has been used includes threaded connections for securing the implant to the holder. These threaded assemblies may also incorporate vertical grooves to further secure the implant. One drawback to threaded connections includes cross-threading and the resulting difficulties in placing the implant in the desired position. Another type of insertion tool assembly that has been used includes parallel vertical jaws for securing the implant to the assembly. These jaws may, for example, protrude into upper and lower keels on the implant. One drawback to the parallel jaws is that the jaws may have issues maintaining parallelism with regards to the upper and lower endplates in certain artificial discs.

Thus, there is a need for improved insertion tool assemblies that can securely hold the implant while placing the implant within the patient.

SUMMARY

A packaging insert/cartridge for use with an implant having first and second components is provided. The packaging insert includes a main body, a snap fit latch extending proximally from the main body, the snap fit latch adapted to snap fit over a mating part of an implant inserter, and at least one spacer extending distally from the main body and configured to be disposed between the first and second components of the implant.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

These drawings illustrate certain aspects of the present invention and should not be used to limit or define the invention.

DETAILED DESCRIPTION OF THE ILLUSTRATED EMBODIMENTS

Embodiments of the present invention provide insertion tool assemblies that can be used to position an implant at a target location within a patient. Non-limiting examples of implants that may be used with the assemblies include spinal implants, such as spacers, artificial discs, and plates among others. Advantageously, the insertion tool assemblies should rigidly fix the implant to the assembly during insertion of the implant into the patient in accordance with embodiments of the present invention. Accordingly, the implant should generally remain fixed to embodiments of the assemblies during impaction and maneuvering when being used by the surgeon, for example. In certain embodiments, the insertion tool assemblies should be able to rigidly fix the implant to the assembly in embodiments where there is little surface area on the implant for gripping by the assembly. This may be particularly beneficial with certain implants, such as artificial discs.

Figure 1:
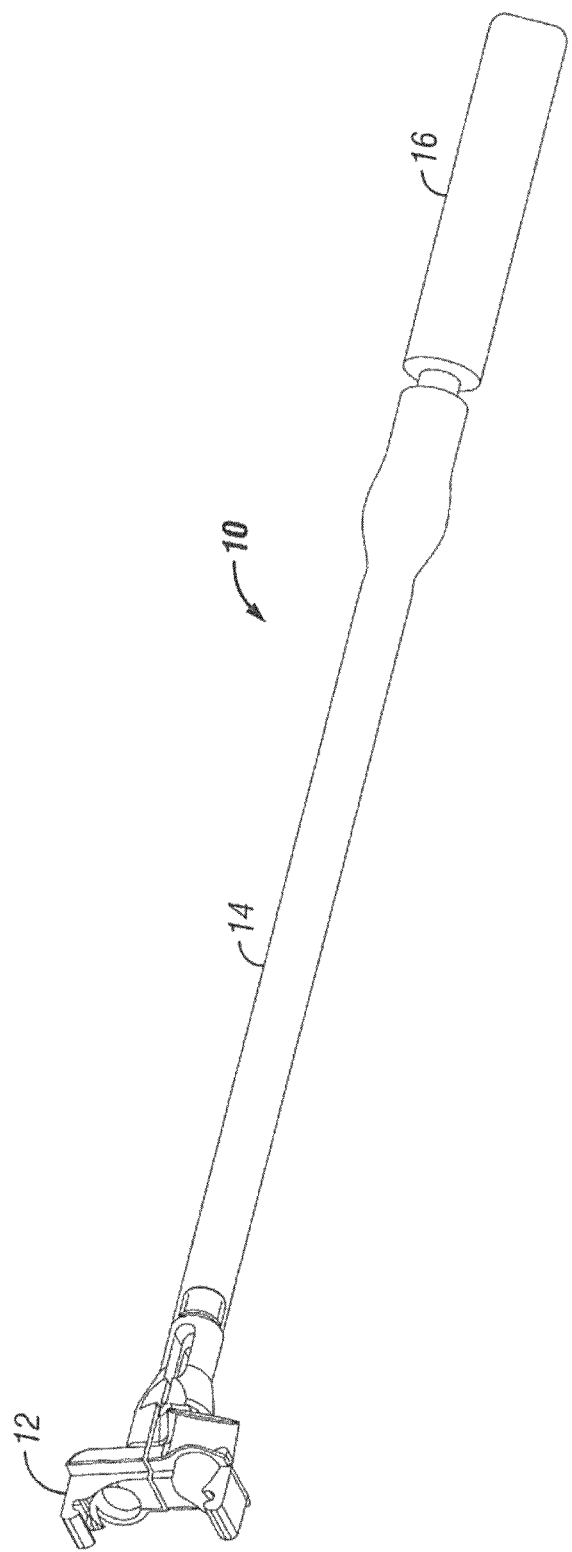
FIG. 1 illustrates an insertion tool assembly in accordance with one embodiment of the present invention.
Figure 2:
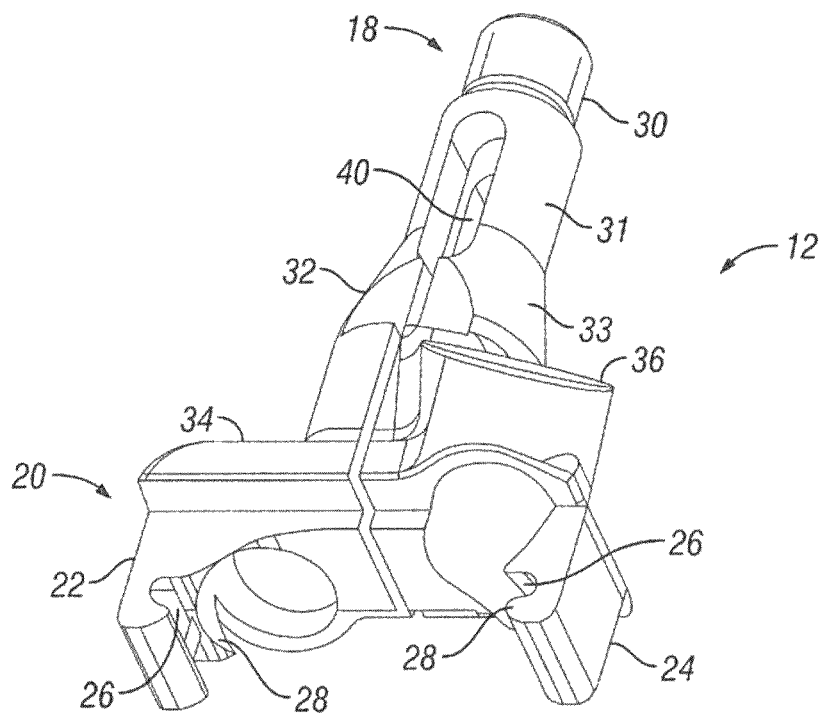
FIG. 2 is a perspective view of a gripping tip of an insertion tool assembly in accordance with one embodiment of the present invention.
Figure 3:
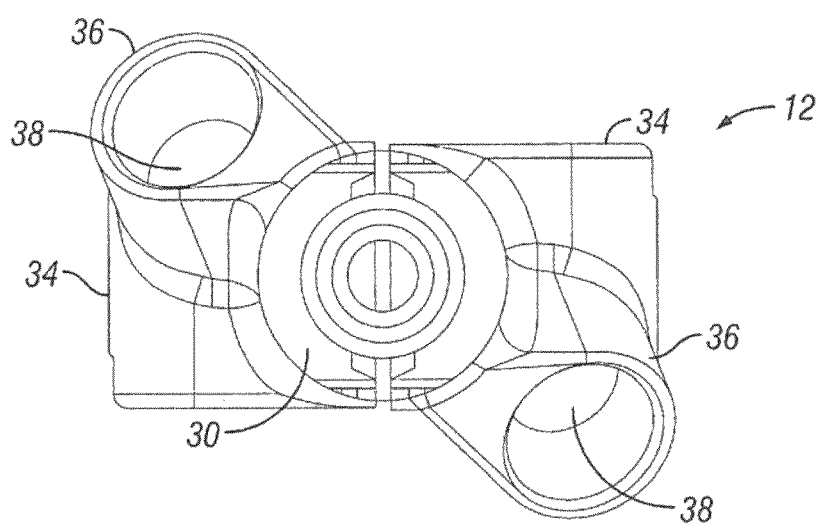
FIG. 3 is an end view of a gripping tip of an insertion tool assembly in accordance with one embodiment of the present invention.
Figure 4:
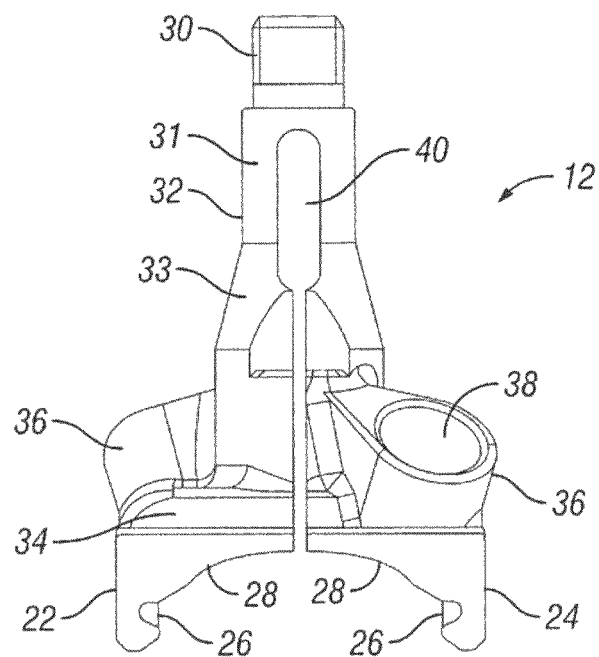
FIGS. 4 and 5 are side views of a gripping tip of an insertion tool assembly in accordance with one embodiment of the present invention.
Figure 5:
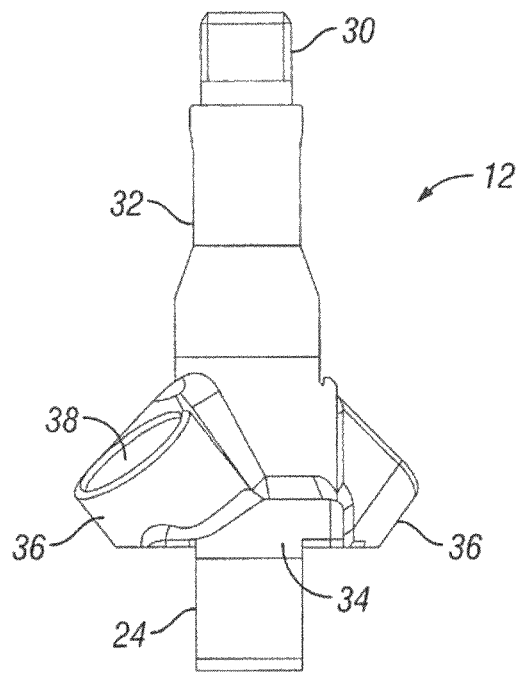

FIG. 1 illustrates an insertion tool assembly 10 in accordance with one embodiment of the present invention. As illustrated, the insertion tool assembly 10 may comprise a gripping tip 12, a sleeve assembly 14, and a handle assembly 16. The gripping tip 12 should generally be configured to engage an implant and fixedly couple the implant to the insertion tool assembly 10. When a physician has maneuvered the implant to a desired location with the patient, the gripping tip 12 should be configured to release the implant. The gripping tip 12 is generally coupled to a sleeve assembly 14 that is disposed between the gripping tip 12 and the handle assembly 16 in the illustrated embodiment. In accordance with the present embodiments, the sleeve assembly 14 may comprise one or more tubes or sleeves. As illustrated, the handle assembly 16 may be coupled to the sleeve assembly 14. In an embodiment, a physician may engage the handle assembly 16 to maneuver the implant to a target location with the patient.

FIGS. 2-5 illustrate a gripping tip 12 for an insertion tool assembly 10 (see, e.g., FIG. 1) having a proximal end 18 and a distal end 20 in accordance with one embodiment of the present invention. In the illustrated embodiment, the distal end 20 of the gripping tip 12 includes a first jaw portion 22 and second jaw portion 24. The first and second jaw portions 22, 24 may be configured to close to fixedly secure the implant to the insertion tool assembly 10. The gripping tip 12 may further include a keyed protrusion 26. As illustrated, each of the first and second jaw portions 22, 24 may include a keyed protrusion 26 on an interior surface 28 of the jaw portions 22, 24 that engage the implant. In certain embodiments, the keyed protrusion 26 may be configured to engage with a corresponding guide or recess on the implant so that the implant can be fixed to the insertion tool assembly 10 as desired. In an embodiment, the guide/recess on the implant should be capable of engaging with the keyed protrusion 26 at only one angle and orientation. The proximal end 18 of the gripping tip 12 may include a threaded portion 30 for coupling the gripping tip 12 to the sleeve assembly 14. The gripping tip 12 may include a body portion 32 disposed between the first and second jaw portions 22, 24 and the threaded portion 30. As illustrated, the body portion 32 may be generally cylindrical in shape and also may include an exterior surface 31 having a tapered portion 33.

In accordance with embodiments of the present invention, the gripping tip 12 may further include a flanged portion 34. As illustrated, each of the first and second jaw portions 22, 24 may extend outwardly from the outer edges of the flanged portion 34 in the direction of the longitudinal axis of the gripping tip 12. The flanged portion 34 may include at least one (e.g., two) drill guide 36, which may be attachments to, or openings in, the flanged portion 34. The drill guide 36 should generally be configured to facilitate fixed angle drilling and/or screw insertion, for example. As illustrated, each drill guide 36 may include a hole 38 through which devices (e.g., drills, screws, etc.) can be inserted. In an embodiment, the holes 38 in the drill guides 36 are angled inwardly (e.g., toward one another). As illustrated, one of the holes 38 may be angled upwardly with the other hole 38 angled downwardly.

As illustrated by FIGS. 2-5, the gripping tip 12 may have a slot 40 that extends from the proximal end 18 to the distal end 20 to allow flexing of the tip 12. In the illustrated embodiment, the slot 40 extends from the flanged portion 34 to the body portion 32. In an embodiment, the slot 40 may be open on the distal end 20 of the gripping tip 12. In accordance with embodiments of the present invention, the slot 40 should generally allow flexing of the gripping tip 12 so that the first and second jaw portions 22, 24 can clamp down onto an implant or release the implant. As illustrated, the slot may narrow in the tapered portion 33 of the body portion 32.

Figure 6:
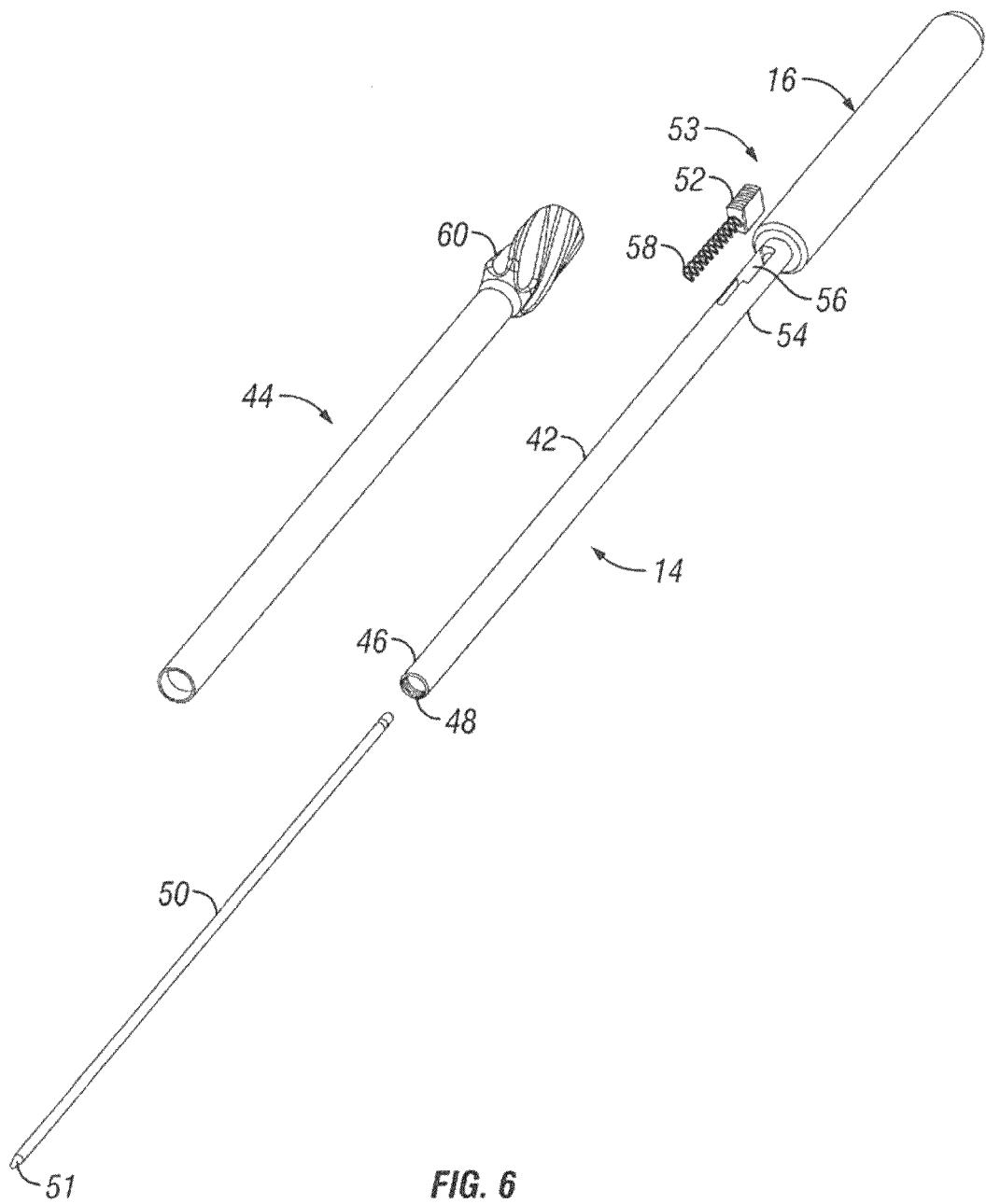
FIGS. 6 and 7 are exploded views of a sleeve assembly and handle assembly for an insertion tool assembly in accordance with one embodiment of the present invention.
Figure 7:
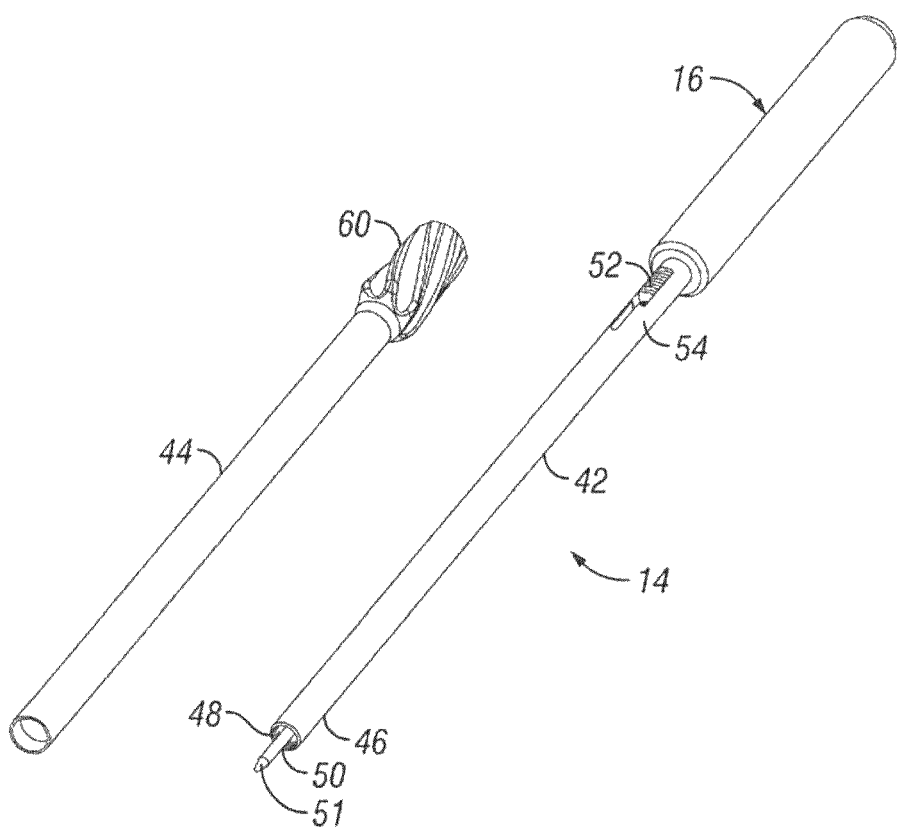

FIGS. 6 and 7 illustrate exploded views of the sleeve assembly 14 and handle assembly 16 for an insertion tool assembly 10 (see, e.g., FIG. 1) in accordance with one embodiment of the present invention. FIGS. 8-13 illustrate additional views of the sleeve assembly and handle assembly 16 in accordance with embodiments of the present invention. As illustrated, the sleeve assembly 14 includes an inner sleeve 42 and an outer sleeve 44 that is disposed over the inner sleeve 42 when assembled with the inner sleeve 42 generally configured for attachment to the gripping tip 12. In an embodiment, the distal end 46 of the inner sleeve 42 contains threads 48 for forming a threaded connection with the threaded portion 30 of the gripping tip 12. As illustrated, the outer sleeve 44 may be configured to move along the outer surface of the inner sleeve 42. As will be discussed in more detail below with respect to FIGS. 8-11, the outer sleeve 44 may move down the inner sleeve 42 to lock the gripping tip 12 onto the implant in accordance with embodiments of the present invention.

Figure 10:
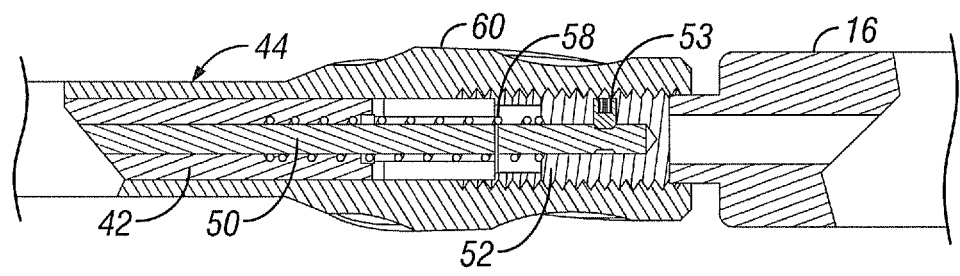
FIG. 10 is a partial cross-sectional view of the proximal end of an insertion tool assembly in the locked position in accordance with one embodiment of the present invention.
Figure 11:
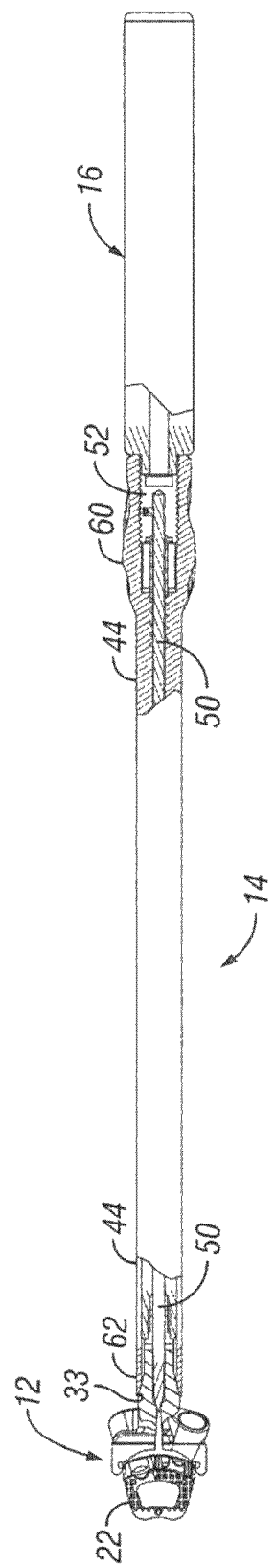
FIG. 11 is a partial cross-sectional view of an insertion tool assembly in the unlocked position in accordance with one embodiment of the present invention.
Figure 12:
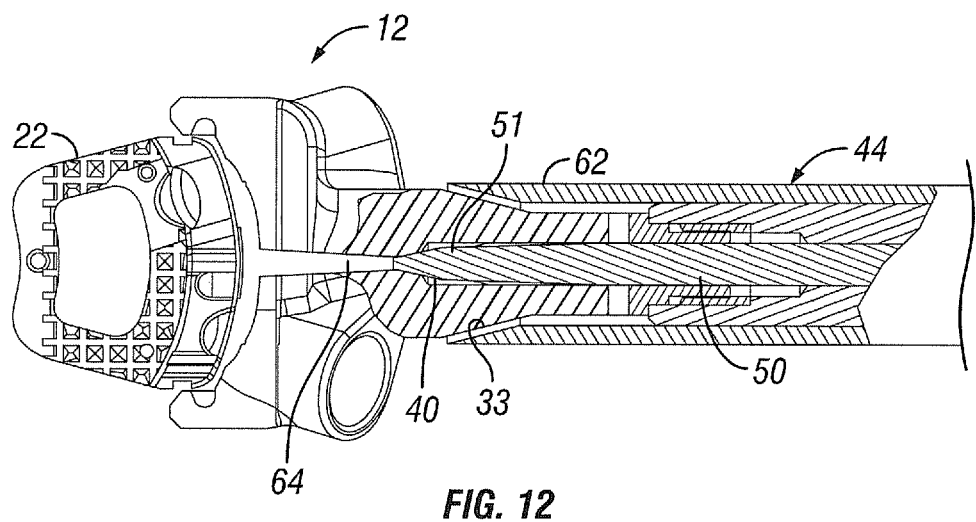
FIG. 12 is a partial cross-sectional view of the distal end of an insertion tool assembly in the unlocked position in accordance with one embodiment of the present invention.
Figure 13:
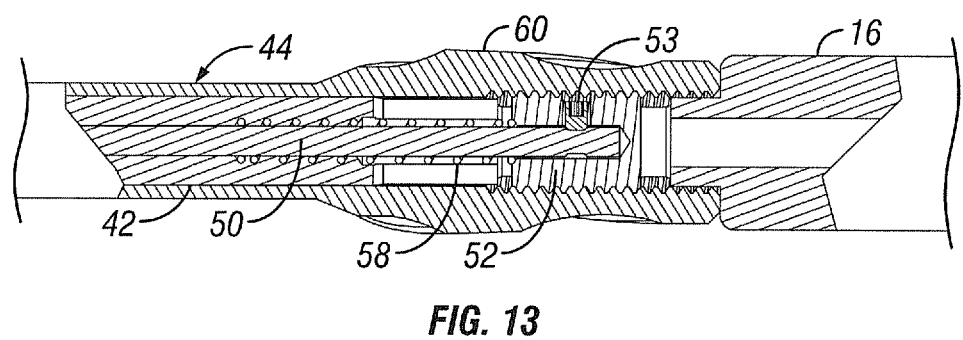
FIG. 13 is a partial cross-sectional view of the proximal end of an insertion tool assembly in the unlocked position in accordance with one embodiment of the present invention.

In the illustrated embodiment, the sleeve assembly 14 further includes a plunger 50 that is disposed inside the inner sleeve 42. The plunger 50 may include, for example, a tip 51 that extends through the distal end 46 of the inner sleeve 42. As illustrated, the plunger 50 may be coupled to a threaded nut 52. A set screw 53, for example, may be used to fix the plunger 50 to the threaded nut 52. The threaded nut 52 may be disposed in the proximal end 54 of the inner sleeve 42. In the illustrated embodiment, the inner sleeve 42 includes at least one (e.g., two) slot 56 in its proximal end 54 through which the exterior threads of the threaded nut 52 extend. The slot 56 allows for translation of the threaded nut 52 within the inner sleeve 42. As illustrated by FIG. 10, the proximal end 60 of outer sleeve 44 can be threaded onto the threads of the threaded nut 52. The sleeve assembly 14 may further include a spring 58 in the inner sleeve 42 with the spring 58 engaging the threaded nut 52, in accordance with an embodiment. In an embodiment, the spring 58 provides force to maintain engagement between the threaded nut 52 and the handle assembly 16. In other words, the spring 58 prevents the threaded nut 52 from freely sliding within the inner sleeve 42 and pushes the nut 52 toward the proximal end of the slot 56 in the inner sleeve 42.

Figure 8:
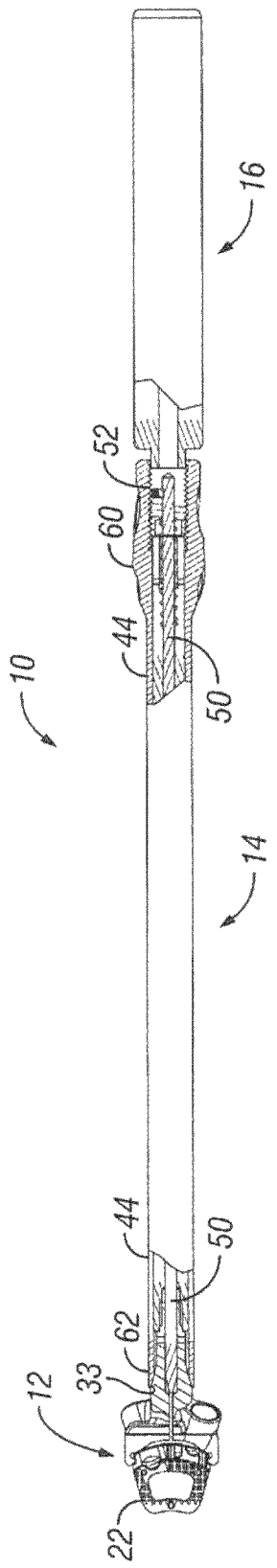
FIG. 8 is a partial cross-sectional view of an insertion tool assembly in the locked position in accordance with one embodiment of the present invention.
Figure 9:
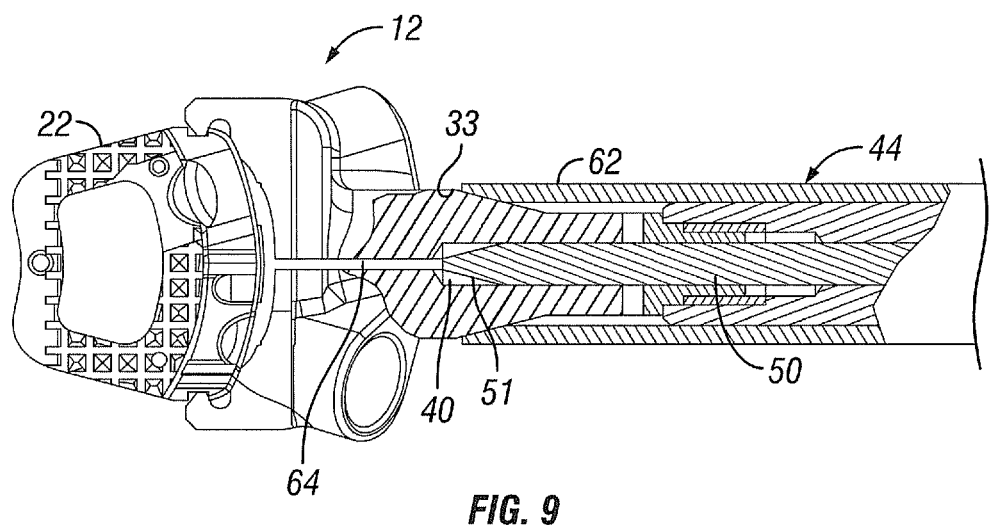
FIG. 9 is a partial cross-sectional view of the distal end of an insertion tool assembly in the locked position in accordance with one embodiment of the present invention.

FIGS. 8-10 illustrate the insertion tool assembly 10 (see, e.g., FIG. 1) with the gripping tip 12 in a locked position in accordance with one embodiment of the present invention. The insertion tool assembly 10 may be placed in the locked position, for example, to secure the gripping tip 12 to an implant. To place the insertion tool assembly 10 in a locked position in accordance with one embodiment, the outer sleeve 44 can be forced down the inner sleeve 42 and onto the gripping tip 12. As the distal end 62 of the outer sleeve engages the beveled surface 33 of the gripping tip 12, the gripping tip 12 should flex closing the first and second jaw portions 22, 24 onto the implant. In this manner, the implant may be rigidly fixed to the insertion tool assembly 10 in accordance with one embodiment of the present invention. The surgeon may then maneuver the implant to the desired position in the patient, for example.

In the embodiment illustrated by FIGS. 8-10, the plunger 50 is disposed in the slot 40 of the gripping tip 12 when the insertion tool assembly 10 is in the locked portion. As illustrated, the slot 40 includes a narrow portion 64 having a diameter less than the diameter of the plunger 50. In an embodiment, the narrow portion 64 is generally in the beveled portion 33 of the gripping tip 12.

FIGS. 11-14 illustrate the insertion tool assembly 10 (see e.g., FIG. 1) with the gripping tip 12 in an unlocked position in accordance with one embodiment of the present invention. The insertion tool assembly 10 may be placed in the unlocked position, for example, to release the implant from the gripping tip 12. The implant may be released from the insertion tool assembly 10, for example, after it has been maneuvered to the desired position within the patient. To place the insertion tool assembly 10 in an unlocked position in accordance with one embodiment, the tip 51 of the plunger 50 can be forced into the narrow portion 64 of the slot 40. This should cause the gripping tip 12 to flex outwardly forcing open the first and second jaw portions 22, 24 releasing the implant. In an embodiment, the plunger 50 may be forced further into the slot 40 by tightening the outer sleeve 44 against the handle assembly 16. As illustrated, tightening the outer sleeve 44 may engage the threaded nut 52 such that tightening the outer sleeve 44 should force the threaded nut 52 and, thus, the plunger 50, further down the inner sleeve 42. It should be understood that other suitable techniques for forcing the plunger 50 further into the slot 40 may be used in accordance with embodiments of the present invention.

Figure 14:
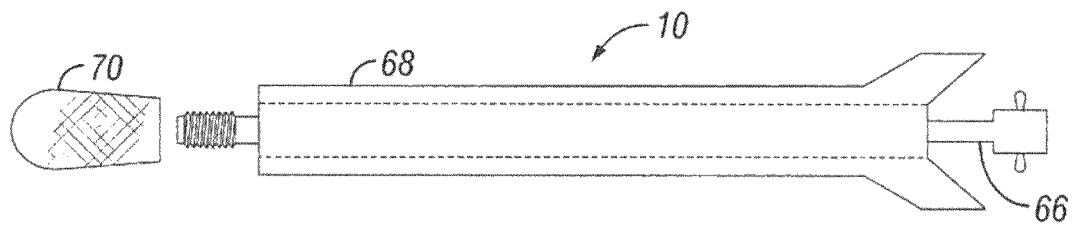
FIG. 14 is a side view of an insertion tool assembly in accordance with one embodiment of the present invention.
Figure 15:
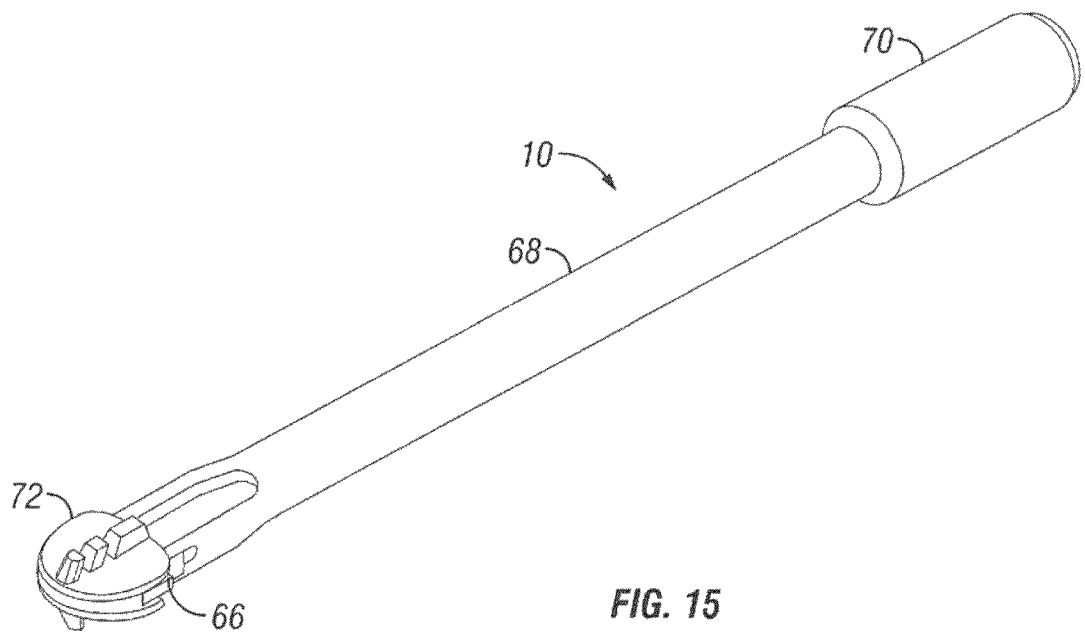
FIG. 15 is a perspective view an insertion tool assembly holding an implant in accordance with one embodiment of the present invention.

FIGS. 14 and 15 illustrate an insertion tool assembly 10 in accordance with another embodiment of the present invention. As illustrated, the insertion tool assembly 10 may comprise a retractable insertion device 66, a sleeve 68 disposed over the retractable insertion device 66, and a handle 70. As illustrated by FIG. 15, the retractable insertion device 66 may hold an implant 72 while the implant 72 is gripped between ends of the sleeve 68. Operation of the insertion tool assembly 10 for holding the implant 72 will be described in more detail with reference to the following figures.

Figure 16:
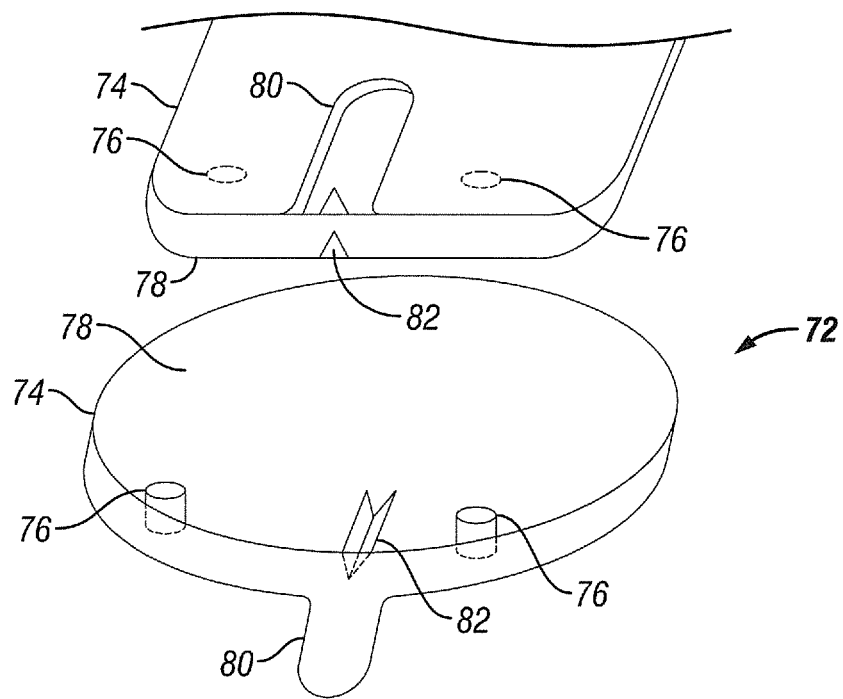
FIGS. 16 and 17 illustrate views of an implant for use with an insertion tool assembly in accordance with one embodiment of the present invention.
Figure 17:
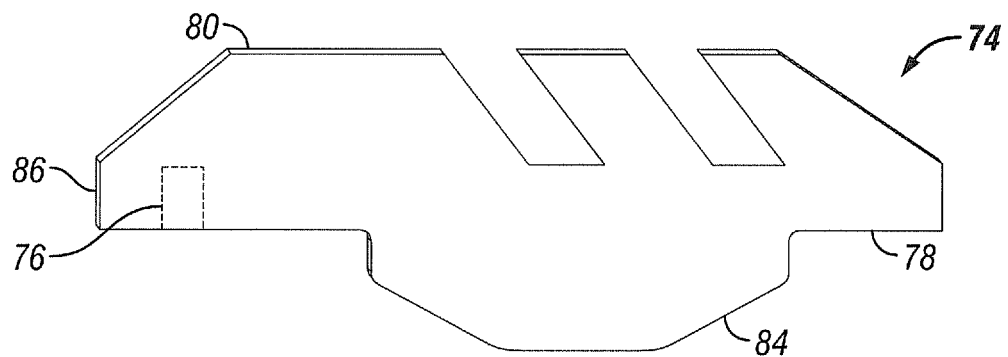

As previously mentioned, insertion tool assemblies of the present invention may be used with a wide variety of implants, such as spacers and artificial discs. FIGS. 16 and 17 illustrate an implant 72 (e.g., an artificial disc) that can be used with insertion tool assembly 10. In an embodiment, the implant 72 may be used, for example, with the insertion tool assembly 10 illustrated by FIGS. 14 and 15. As illustrated, the implant 72 may comprise endplates 74. Each of the endplates 74 may comprise one or more (e.g., two) holes 76 in the inner face 78. In the illustrated embodiment, the holes 76 are blind holes. As illustrated, each of the endplates may further comprise at least one (e.g., two) keel 80. In an embodiment, the inner face 78 of each of the endplate 74 contains an alignment groove 82. In addition, the inner face 78 of each endplate may also contain protruding portion 84, which as illustrated by FIG. 17 may be rounded. In an embodiment, the holes 76 may be disposed in the inner face 78 between the protruding portion 84 and the anterior end 86.

Figure 18:
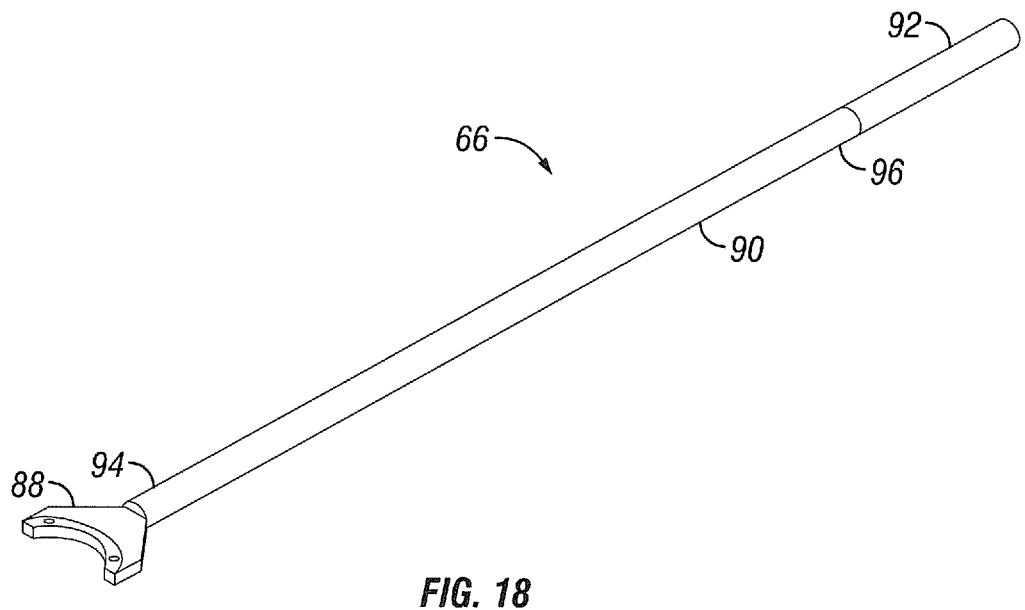
FIG. 18 is a perspective view of an insertion device for an insertion tool assembly in accordance with one embodiment of the present invention.
Figure 19:
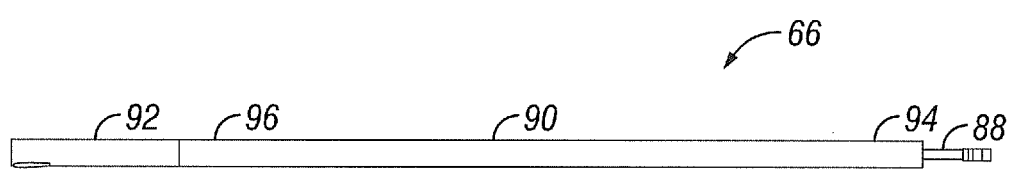
FIG. 19 is a side view of an insertion device for an insertion tool assembly in accordance with one embodiment of the present invention.

FIGS. 18 and 19 illustrate a retractable insertion device 66 for an insertion tool assembly 10 (see, e.g., FIGS. 15 and 16) in more detail in accordance with one embodiment of the present invention. As illustrated, the retractable insertion device 66 may comprise a holding device 88, a rod portion 90, and a threaded portion 92. The holding device 88 may be disposed on the distal end 94 of the rod portion 90. As will be discussed in more detail below, the holding device 88 may be configured to interlock with an implant, such as implant 72 on FIGS. 16 and 17. The threaded portion 92 may be disposed on the proximal end 96 of the rod portion 90. In an embodiment, the threaded portion 92 may be configured to threadedly connect with the handle 70 (see, e.g., FIG. 14).

Figure 20:
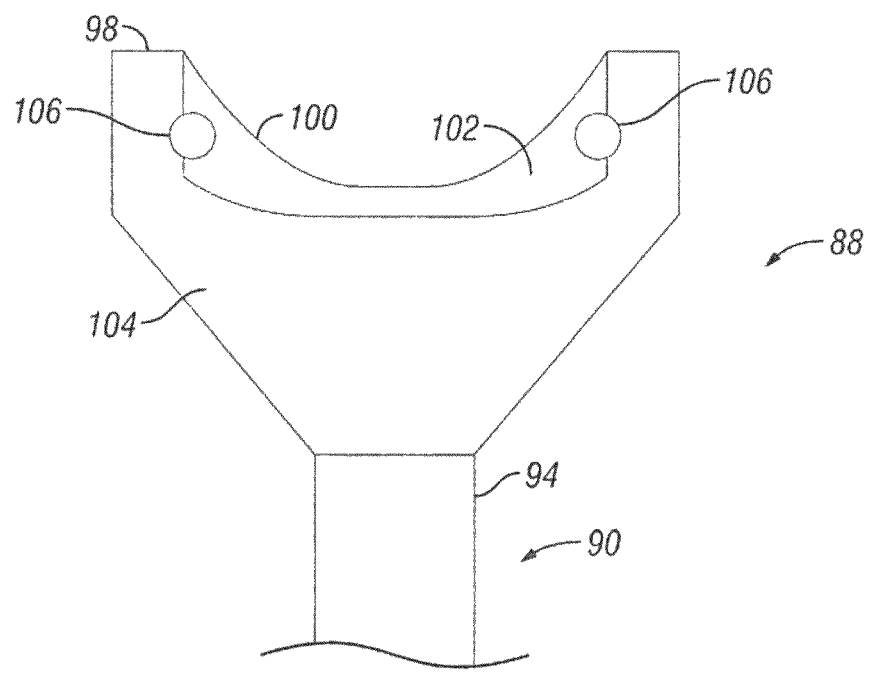
FIG. 20 is a top view of a holding mechanism for an insertion tool assembly in accordance with one embodiment of the present invention.

FIG. 20 illustrates a holding device 88 for an insertion device 66 (see, e.g., FIGS. 18 and 19) in accordance with one embodiment of the present invention. The insertion device 66 may be coupled to the distal end 94 of the rod portion 90. In the illustrated embodiment, the holding device 88 may be generally paddle shaped. As illustrated, the outer edge 98 of the holding device 88 may have a concave portion 100. However, it should be understood that the alternate embodiments may include an outer edge that is straight or convex, for example. In an embodiment, the concave portion 100 of the outer edge 98 has a beveled surface 102. The upper face 104 of the holding device 88 may comprise one or more (e.g., two) holes 106 for receiving pins (e.g., pins 108 on FIG. 21). In an embodiment, the holes 106 are blind holds. In certain embodiments, the pins may be configured to engage with corresponding holes in the implant (e.g., holes 76 on FIGS. 16 and 17). While not illustrated, the holding device 88 may comprise a lower face that is similar to the upper face 104 in that the lower face may include one or more holes for receiving pins that interlock the holding device 88 with an implant in accordance with one embodiment of the present invention. For example, the pins in the upper face 104 may be configured to engage with holes 76 in the inner face 78 of an endplate 74 (see, e.g., FIG. 14) while the lower face may interlock with holes 76 in the inner face 78 of the opposing endplate 74 (see, e.g., FIG. 14), securing the implant 72 to the holding device 88. In an embodiment, the pins may be configured to retract so that the implant can be released as desired.

Figure 21:
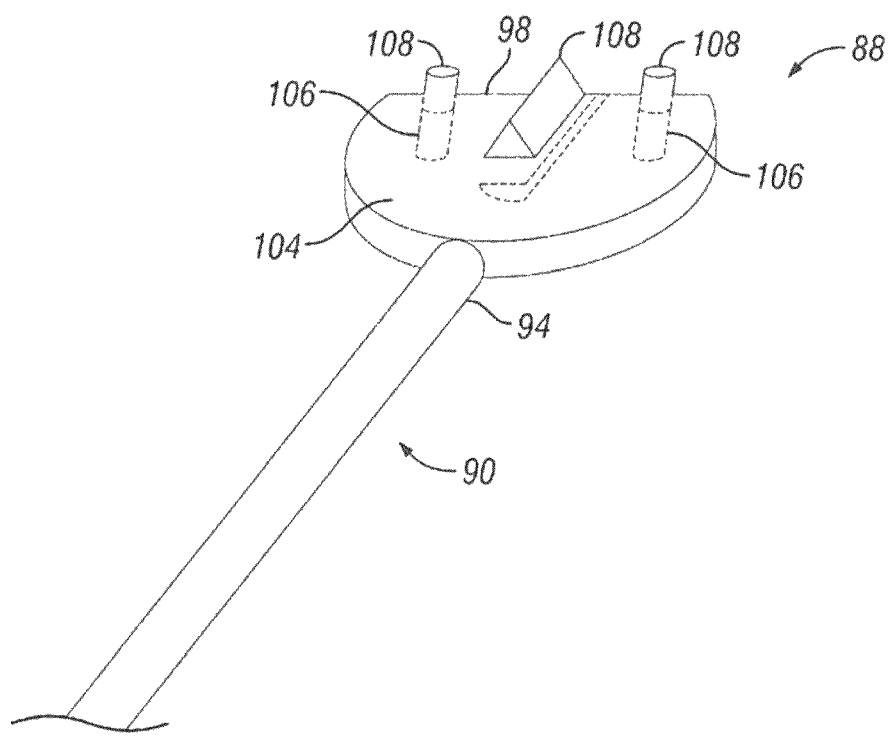
FIG. 21 illustrates another view of a holding mechanism for an insertion tool assembly in accordance with one embodiment of the present invention.

FIG. 21 illustrates another embodiment of a holding device 88 for an insertion device 66 (see, e.g., FIGS. 18 and 19). The holding device 88 is similar to the device illustrated on FIG. 19. For example, the holding device 88 is generally paddle shaped and comprises pins 108 in holes 106 for interlocking the insertion device 66 in accordance with embodiments of the present invention. However, rather than having an outer edge 98 with a concave portion 100 as illustrated on FIG. 19, the embodiment of FIG. 20 illustrates an outer edge 98 that is generally straight in shape. In addition, the holding device 88 of this embodiment comprises a wedge 110 that protrudes from the upper face 104 of the holding device 88. In certain embodiments, the wedge 110 may be configured to engage with a corresponding opening in the implant 72 (e.g., alignment groove 82 on FIG. 14) so that the holding device 88 can be fixed to the implant 72 as desired. In an embodiment, the wedge 110 of the holding device 88 is capable of engaging with the alignment groove 82 at only one angle and orientation.

Figure 22:
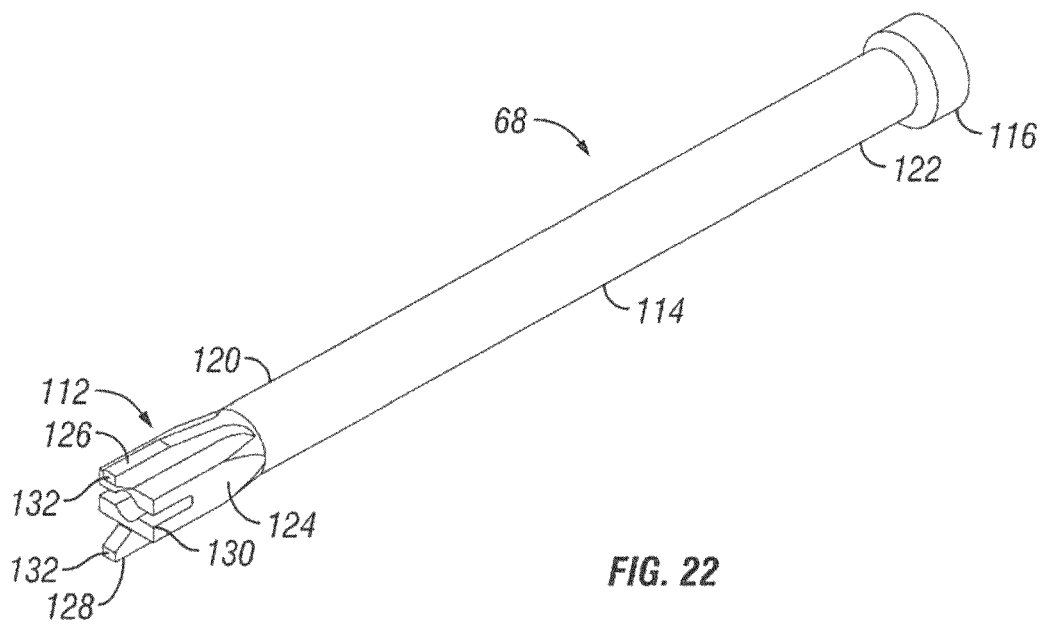
FIG. 22 is a perspective view of a sleeve for an insertion tool assembly in accordance with one embodiment of the present invention.
Figure 23:
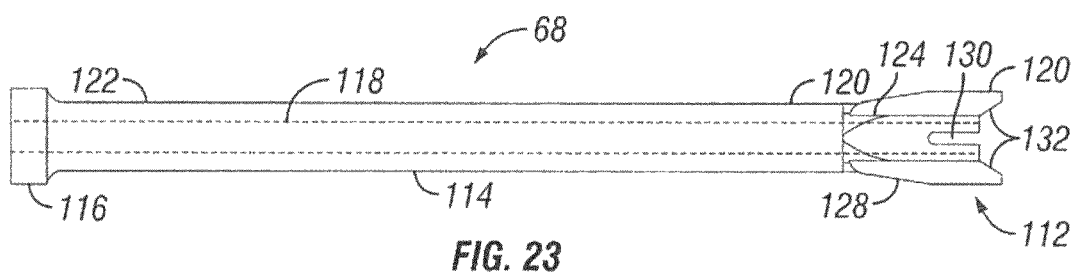
FIG. 23 is a side view of a sleeve for an insertion tool assembly in accordance with one embodiment of the present invention.
Figure 24:
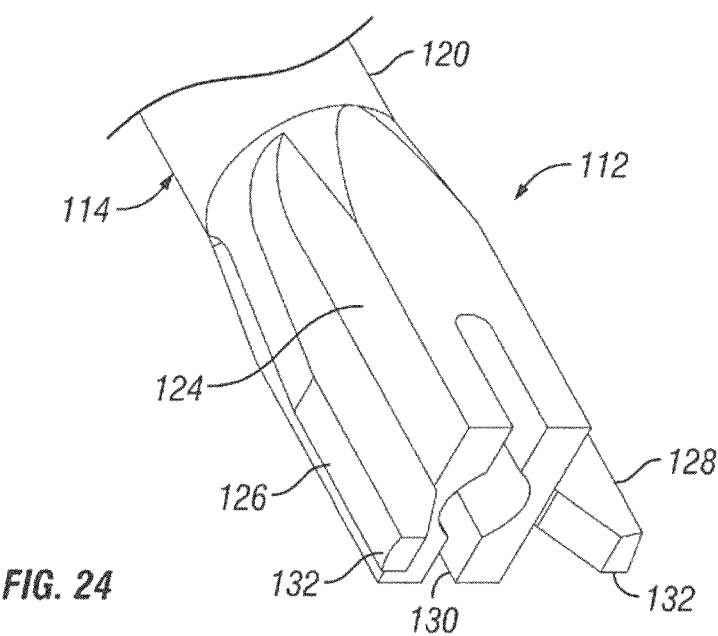
FIG. 24 is a perspective of implant holding jaws for an insertion tool assembly in accordance with one embodiment of the present invention.

FIGS. 22-24 illustrate a sleeve 68 having implant holding jaws 112 in accordance with one embodiment of the present invention. As illustrated, the sleeve 68 comprises implant holding jaws 112, sleeve portion 114, and a flanged end 116. In the illustrated embodiment, the sleeve 68 comprises a throughbore extending 118 longitudinally through the sleeve 68, for example. The implant holding jaws 112 may be disposed on the distal end 118 of the sleeve portion 114. As will be discussed in more detail below, the implant holding jaws 112 may be configured to engage the implant 72 (see, e.g., FIG. 15). The flanged end 116 may be disposed on the proximal end 122 of the sleeve 68.

As illustrated by FIGS. 22-24, the implant holding jaws 112 generally may comprise a body portion 124 having a first jaw portion 126 and a second jaw portion 128. In the illustrated embodiment, the throughbore 118 in the sleeve 68 enlarges to form a slot 130 in the body portion 124 of the implant holding jaws 112. In other words, the entrance to the throughbore 68 is a slot 130 in the body portion 124 of the implant holding jaws 112 in accordance with certain embodiments. Embodiments of the implant holding jaws 112 may comprise a first jaw portion 126 and second jaw portion 128 configured to engage an implant. For example, the first and second jaw portions 126, 128 may engage, for example, an upper face of an implant 72 as illustrated by FIG. 15. For example, the first and second jaw portions 126, 128 may be configured to engage an angled portion of the keel extending from the upper face of the implant 72. As illustrated, at least a portion the first and second jaw portions 126, 128 may be protrusions or raised surfaces on opposite sides of the body portion 124 with the jaw tips 130 extending beyond the edge of the body portion 124. In an embodiment, the implant 72 (see, e.g., FIG. 15) is held between the jaw tips 130. In the illustrated embodiment, the jaw tips 130 form a flared opening for receiving the implant 72.

An example method for holding the implant 72 with the insertion tool assembly 10 will be described in more detail with respect to FIGS. 14-24. An embodiment for holding the implant 72 includes coupling the implant 72 to the retractable insertion device 66. Coupling the implant 72 to the retractable insertion device 66 may include disposing one or more pins 108 on an upper face 104 of the retractable insertion device 66 into one or more corresponding holes 76 in an endplate 74 of the implant 72. Coupling the implant 72 further may include disposing one or more pins 108 on a lower face of the retractable insertion device 66 into one or more corresponding holes 76 in another endplate 74 of the implant 72. With the implant 72 coupled to the retractable insertion device 66, the insertion device 66 may be retracted into the sleeve 68. Retracting the insertion device 66 into the sleeve 68 may include rotation of the handle 70. As illustrated by FIG. 18, a portion of the retractable insertion device 66 may retract into the slot 130 in the body portion 124 of the implant holding jaws 112. As the retractable insertion device 66 retracts into the sleeve 68, the implant holding jaws 112 of the sleeve 68 should engage the implant 72. In an embodiment, the implant holding jaws 112 should force together the endplates 74 of the implant 72. In this manner, the implant 72 may be rigidly fixed to the insertion tool assembly 10 in accordance with one embodiment of the present invention. The surgeon may then maneuver the implant 72 to the desired position in the patient, for example.

As previously described with respect to FIGS. 1-13, embodiments of the insertion tool assemblies of the present invention may comprise a gripping tip 12. FIGS. 25-29 illustrate alternative embodiments of a gripping tip 12 that may be used to secure an implant to the insertion tool assembly 10. In an embodiment, the gripping tip 12 illustrated by FIGS. 25-29 may be used with a sleeve assembly 14 and handle assembly 16 as illustrated by FIGS. 1-13. It should be understood, however, that the gripping tip 12 illustrated in these figures may also be used in conjunction with other tube assemblies and handle assemblies in accordance with embodiments of the present invention.

Figure 30:
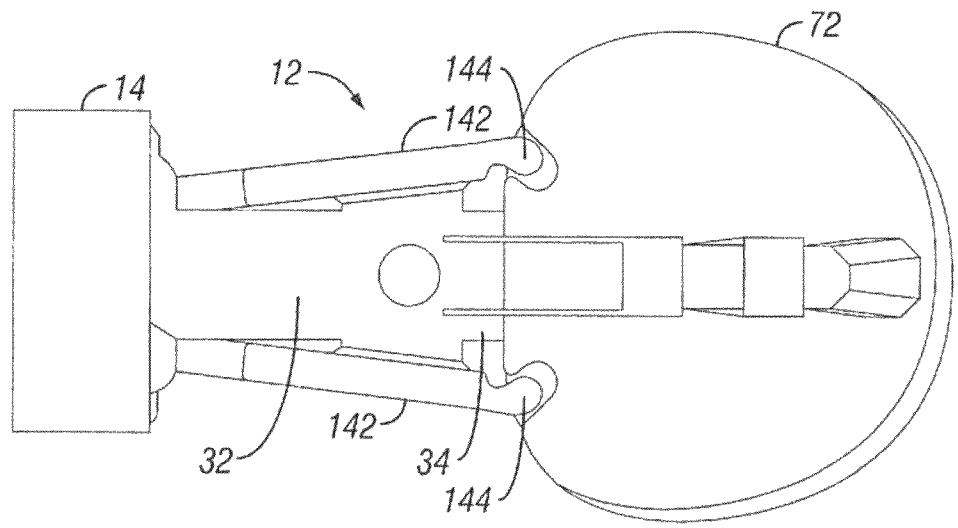
FIG. 30 is a top view of a gripping tip of an insertion tool assembly in a locked position and holding an implant in accordance with one embodiment of the present invention.
Figure 31:
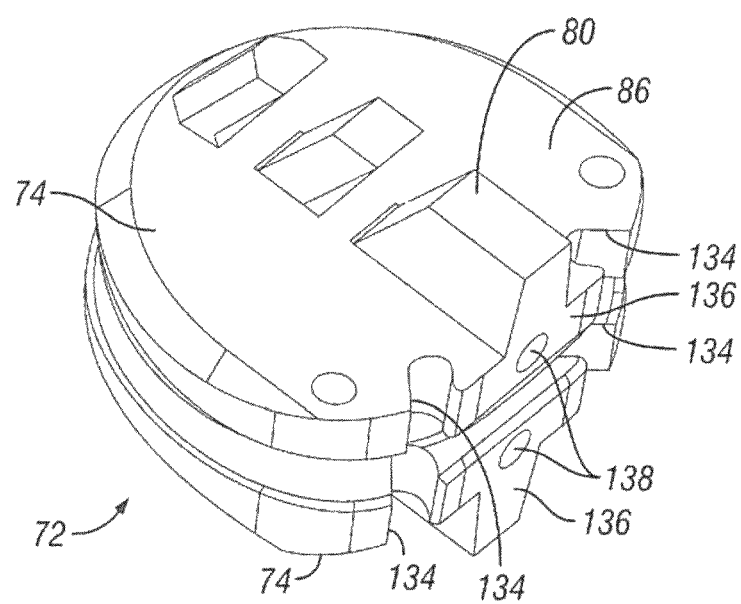
FIG. 31 is a perspective view of an implant for use with an insertion tool assembly in accordance with one embodiment of the present invention.

FIG. 31 illustrates an implant 72 (e.g., an artificial disc) that can be used with insertion tool assembly 10. In an embodiment, the implant 72 may be used, for example, with the insertion tool assembly 10 illustrated by FIGS. 25-30. As illustrated, the implant 72 may comprise endplates 74. Each of the endplates 74 may comprise one or more (e.g., two) lateral slots 134. In the illustrated embodiment, the lateral slots 134 are located on the anterior end 86 of the implant 72. As illustrated, the lateral slots 134 may be symmetrical along the central axis of the implant 72. In an alternate embodiment, one or more (e.g., two) lateral slots 134 may be located in the posterior end of the implant 72 in addition to, or instead of, the lateral slots 134 in the anterior end 86. In addition, the anterior face 136 of each of the endplates 74 may contain one or more (e.g., two) openings 138. Non-limiting examples of the openings 138 include slots, round holes, and square holes. In an alternate embodiment, one or more (e.g., two) openings may be located in the posterior end of the implant 72 in addition to, or instead of, the openings 138 in the anterior end 86. As illustrated, each of the endplates may further comprise at least one (e.g., two) keel 80.

Figure 25:
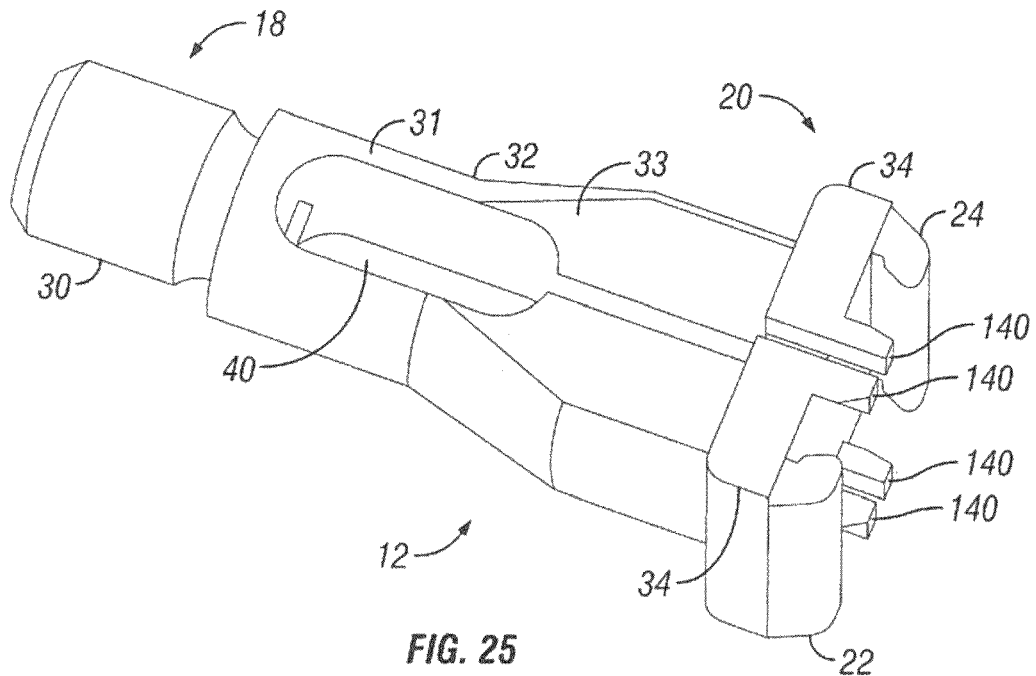
FIG. 25 is a perspective view of a gripping tip of an insertion tool assembly in accordance with one embodiment of the present invention.

FIG. 25 illustrates a gripping tip 12 that may be used to secure an implant to the insertion tool assembly 10 in accordance with one embodiment of the present invention. As illustrated, the gripping tip 12 has a proximal end 18 and a distal end 20 in accordance with one embodiment of the present invention. In the illustrated embodiment, the gripping tip 12 includes a threaded portion 30, a body portion 32, and a flanged portion 34. The threaded portion 30 may be disposed, for example, on the proximal end 18 of the gripping tip 12 for coupling the gripping tip 12 to the sleeve assembly 14. The body portion 32 may be disposed, for example, between the threaded portion 30 and the flanged portion 34. As illustrated, the body portion 32 may be generally cylindrical in shape and also may include an exterior surface 31 having a beveled portion 33.

In the illustrated embodiment, the distal end 20 of the gripping tip 12 may include a first jaw portion 22 and a second jaw portion 24. The first and second jaw portions 22, 24 may be configured to close to fixedly secure the implant to the insertion tool assembly 10. In an embodiment, the first and second jaw portions 22, 24 may be configured to engage with the lateral slots 134 in the endplates 74 of the implant (see, e.g., FIG. 31). As illustrated, the first and second jaw portions 22, 24 may be generally curved or rounded shape. In an embodiment, the first and second jaw portions 22, 24 extend outwardly and longitudinally from the outer edges of the flanged portion 34. One or more (e.g., two, four, etc.) projections 140 may also extend outwardly and longitudinally from the flanged portion 34. As illustrated, the projections 140 may extend outwardly from the flanged portion 34 on the edge of slot 40. The projections 140 may be, for example, round or elliptical pins. The projections 140 may be generally configured to engage with corresponding openings 138 in the implant 72 (see, e.g., the implant 72 illustrated on FIG. 31). In an embodiment, the projections 140 should engage the implant 72 to, for example, stabilize the implant 72 from twisting or being able to articulate.

In the embodiment illustrated by FIG. 25, the gripping tip 12 may have a slot 40 that extends from the proximal end 18 to the distal end 20 to allow flexing of the tip 12. In the illustrated embodiment, the slot 40 extends from the flanged portion 34 to the body portion 30. In an embodiment, the slot 40 may open on the distal end 20 of the gripping tip 12. In accordance with embodiments of the present invention, the slot 40 should generally allow flexing of the gripping tip 12 so that the first and second jaw portions 22, 24 can clamp down on an implant 72 or release the implant. For example, the first and second jaw portions 22, 24 may clamp down into the lateral slots 134 of the implant 72. As illustrated, the slot 40 may narrow in the beveled portion 33 of the body portion 32.

Figure 26:
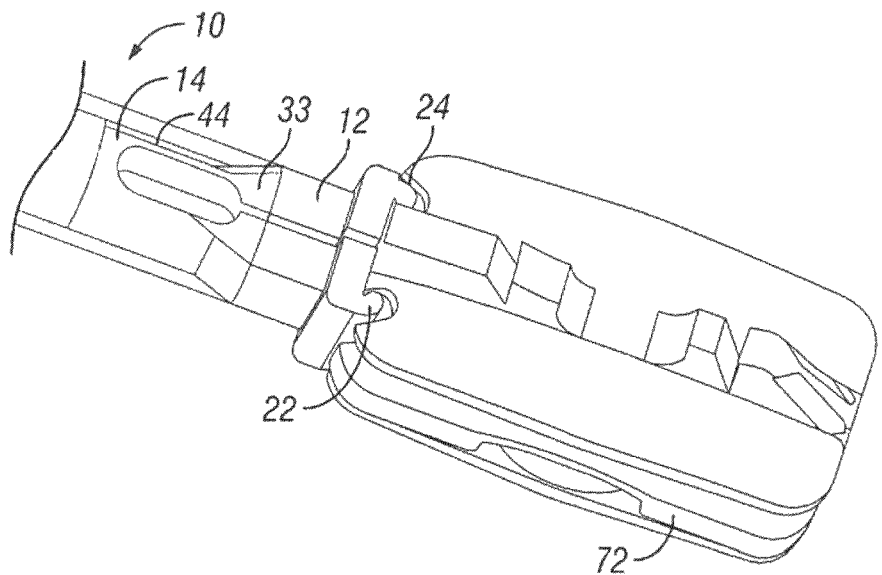
FIG. 26 is a perspective view a gripping tip of an insertion tool assembly in a locked position and holding an implant in accordance with one embodiment of the present invention.

FIG. 26 illustrates the insertion tool assembly 10 of FIG. 25 with the gripping tip 12 in a locked position and holding the implant 72 in accordance with one embodiment of the present invention. The insertion tool assembly 10 may be placed in the locked position, for example, to secure the gripping tip 12 to the implant 72. The implant 72 may be positioned, for example, with the protrusions 140 positioned in the corresponding openings 138 in the implant 72. The outer sleeve 44 of the sleeve assembly 14 may then be forced down and onto the gripping tip 12. As the outer sleeve 44 engages the beveled surface 33 of the gripping tip 12, the gripping tip 12 should flex, clamping the first and second jaw portions 22, 24 into the corresponding lateral slots 134 of the implant 72. In this manner, the implant 72 may be rigidly fixed to the insertion tool assembly 10 in accordance with one embodiment of the present invention. The surgeon may then maneuver the implant 72 to the desired position in the patient, for example. Once the implant has been maneuvered to the desired position within the patient, the implant may be released from the gripping tip. Any of a variety of different techniques may be utilized to cause the insertion tool assembly 10 to release the implant 72 when desired. For example, a plunger 51 (see, e.g., FIG. 6) may be inserted into the slot 40 to force apart the first and second jaw portions 22, 24.

FIGS. 27-30 illustrate a gripping tip 12 that may be used to secure an implant 72 to an insertion tool assembly 10 in accordance with one embodiment of the present invention. As illustrated, the gripping tip 12 includes body portion 32, flanged portion 34, and arms 142. The flanged portion 30 may be disposed on the distal end 20 of the gripping tip 12. In the illustrated embodiment, the gripping tip 12 has one or more (e.g., two) arms 142 coupled to the body portion 32. As illustrated, the gripping tip 12 may include two arms 142 on opposing sides of the body portion 32. The arms 142 may be movably coupled to the body portion 32. Each of the arms 142 may include a jawed end 144. The arms 42 may be configured to swing closed forcing the jawed ends 144 to clamp onto the implant 72 securing the implant 72 to the insertion tool assembly 10. In an embodiment, the jawed ends 144 may be configured to engage with the lateral slots 134 in the endplates 74 of the implant 72. As illustrated, the jawed ends 144 may be generally curved or rounded in shape. One or more (e.g., two) projections 140 may extend outwardly and longitudinally from the flanged portion 34. The projections 140 may be, for example, round or elliptical pins. The projections 140 may be generally configured to engage with corresponding openings 138 in the implant 72. In an embodiment, the projections 140 should engage the implant 72 to, for example, stabilize the implant 72 from twisting or being able to articulate.

Figure 27:
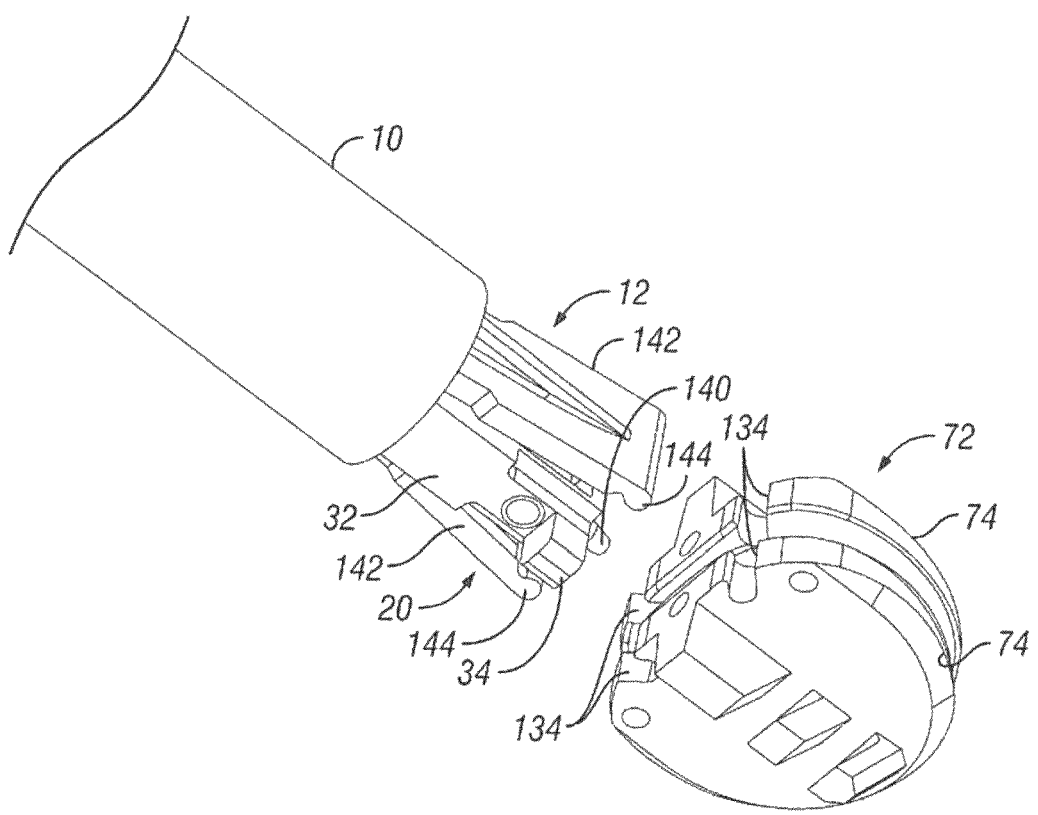
FIG. 27 is a perspective view a gripping tip of an insertion tool assembly and an implant in accordance with one embodiment of the present invention.
Figure 28:
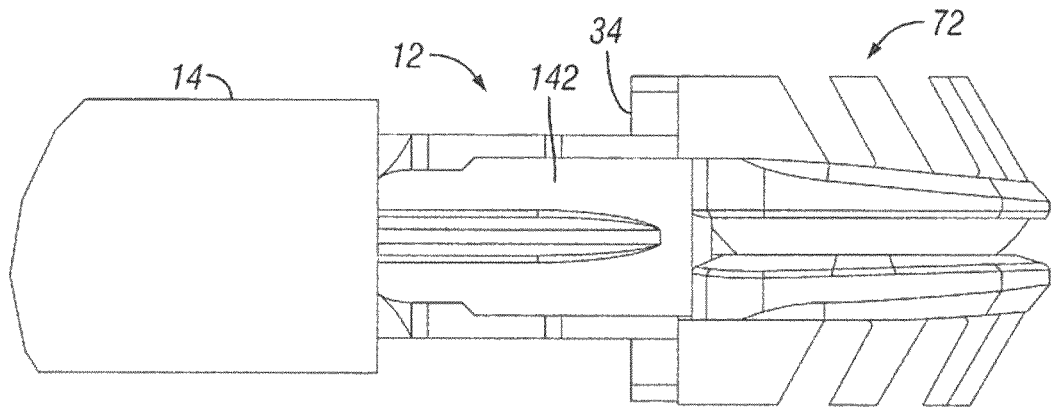
FIG. 28 is a side view of a gripping tip of an insertion tool assembly in a locked position and holding an implant in accordance with one embodiment of the present invention.
Figure 29:
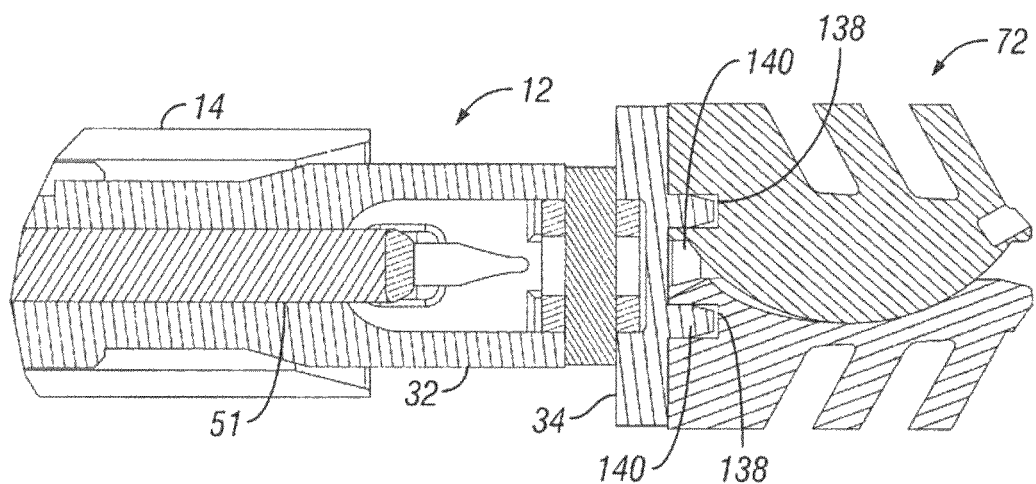
FIG. 29 is a side, cross sectional view of a gripping tip of an insertion tool assembly in a locked position and holding an implant in accordance with one embodiment of the present invention.

FIGS. 28-30 illustrate the insertion tool assembly 10 with the gripping tip 12 of FIG. 27 in a locked position and holding the implant 72 in accordance with one embodiment of the present invention. The insertion tool assembly 10 may be placed in the locked position, for example, to secure the gripping tip 12 to the implant 72. The implant 72 may be positioned, for example, with the protrusions 140 positioned in the corresponding openings 138 in the implant 72. The arms 142 may then be actuated to swing closed. By way of example, a plunger 51 from the sleeve assembly 14 may be pushed into the body portion 32 to force the arms 142 to swing closed. As the arms 142 swing closed, the jawed ends 144 of the arms 142 should to clamp down on the implant 72 in the lateral slots 134. In this manner, the implant 72 may be rigidly fixed to the insertion tool assembly 10 in accordance with one embodiment of the present invention. The surgeon may then maneuver the implant 72 to the desired position in the patient, for example. Once the implant has been maneuvered to the desired position within the patient, the implant may be released from the gripping tip. Any of a variety of different techniques may be utilized to cause the insertion tool assembly 10 to release the implant 72 when desired. For example, the plunger 51 may be removed from the body portion 32 to release the arms 142 causing them to swing open.

Figure 32:
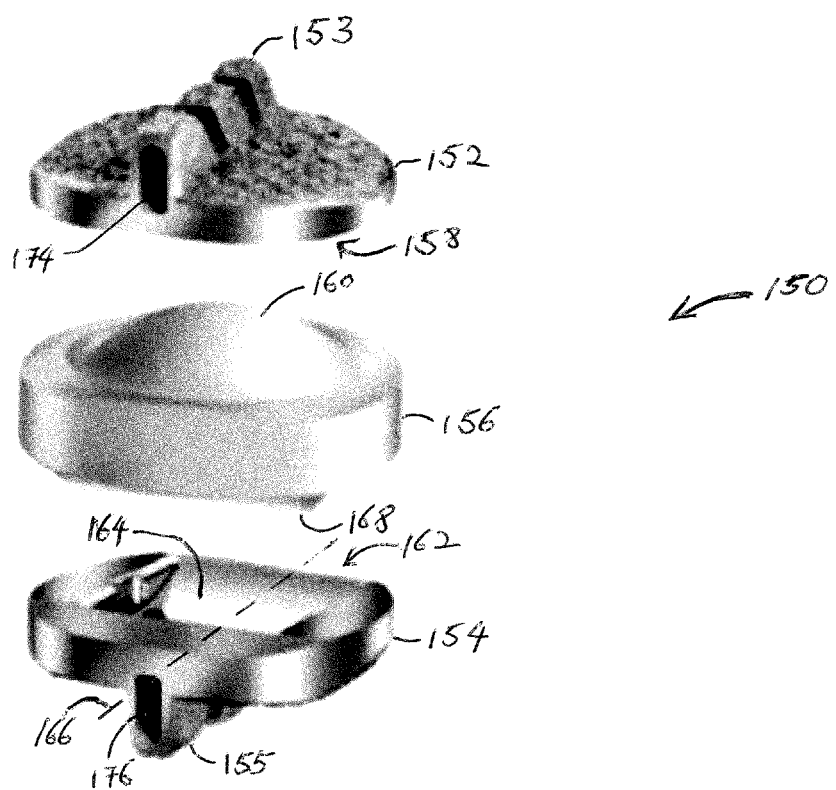
FIG. 32 is a perspective view of a cervical implant according to another aspect of the present invention.

A cervical implant 150 of FIG. 32 is similar to the implant 72 as shown in FIG. 27. The implant 150 includes a superior endplate/component 152 having an upper keel 153 for insertion into a vertebral body, an inferior endplate/component 154 having a lower keel 155 for insertion into a lower adjacent vertebral body, and a core 156 disposed between the two endplates.

The underside 158 of the superior endplate 152 has a spherical recess that interfaces with a spherical shape 160 of the core 156 on its upper side. This provides the superior endplate 152 with three degrees of freedom motion (i.e., pitch, roll and yaw) relative to the core 156 and inferior endplate 154.

An upper side 162 of the inferior endplate 154 has a cylindrical recess 162 running along a central longitudinal axis 166 of the implant 150. The recess 162 has a rectangular outer perimeter and a circular underside that interfaces with a convex cylindrical shape 168 of the core 156 on its underside. Due to a rectangular outer shape in the outer perimeter of the recess 162, the core 156 only has one degree of freedom motion (i.e., pitch) relative to the inferior endplate 154.

Insertion opening 174,176 located at a proximal end of the superior and inferior are designed to receive tips of an implant inserter 214 described later herein for firmly grabbing and implanting the implant 150 into the appropriate vertebral bodies.

Figure 33A:
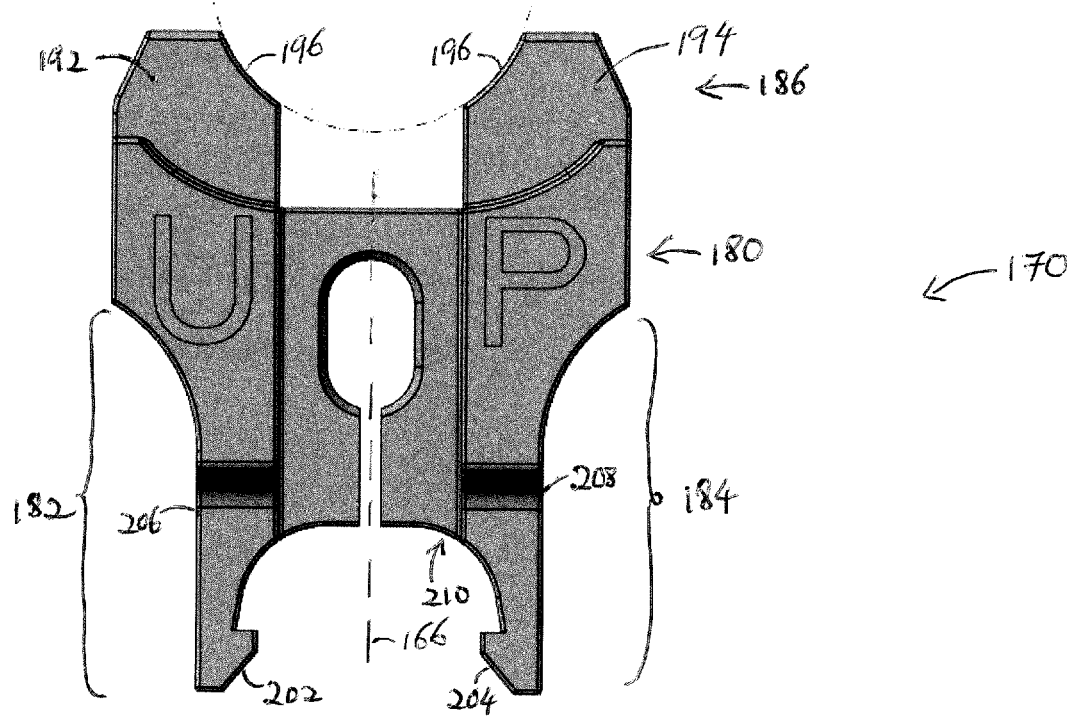
FIG. 33A is a plan view of a packaging insert for the cervical implant of FIG. 32 according to another aspect of the present invention.
Figure 33B:
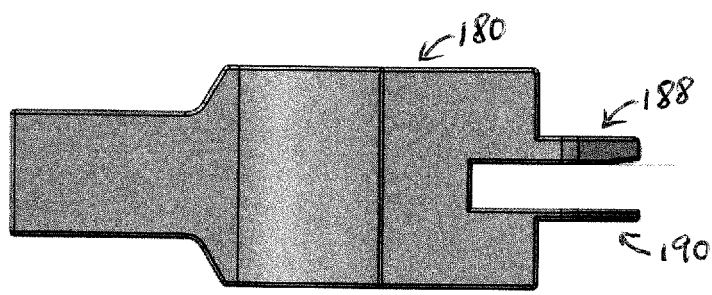
FIG. 33B is a side view of the packaging insert of FIG. 33A.
Figure 33C:
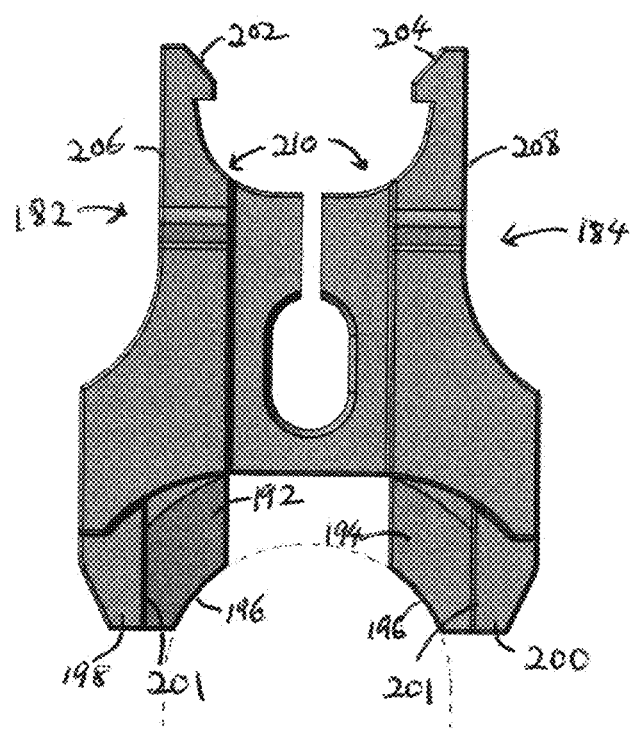
FIG. 33C is a bottom view of the packaging insert of FIG. 33A.
Figure 34:
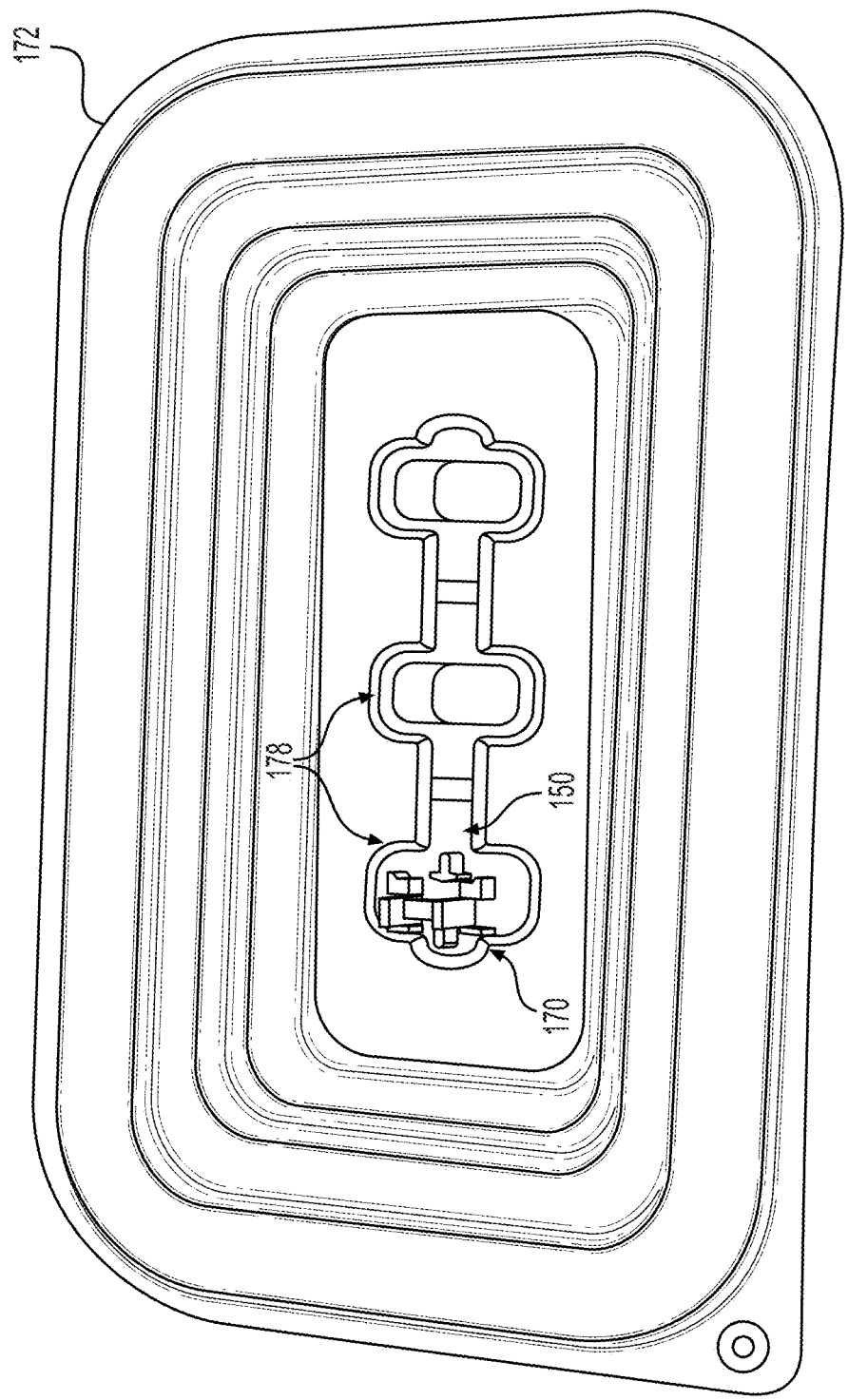
FIG. 34 is a perspective view of an external packaging for storing a plurality of implants of FIG. 32 and packaging inserts.

A packaging insert/cartridge 170 as shown in FIGS. 33A-33C is designed to be used and packaged with the implant 150. As shown in FIG. 34, an external packaging 172 has multiple slots 178 for storing implants 150 with the packaging insert 170 pre-assembled therein. The insert 170 is designed to hold the implant 150 in a neutral orientation while it is being held by an insertion tool and being inserted into the vertebral bodies.

The packaging insert 170 includes a main body 180, first and second snap-fit latches 182, 184 extending proximally from the main body 180, and a spacer 186 extending distally from the main body and configured to be disposed between the superior and inferior endplates 152,154 of the implant 150. The spacer 186 as shown in FIGS. 33A-33C has a superior spacer 188 configured to be disposed between the core 156 and the superior endplate 152 and an inferior spacer 190 configured to be disposed between the core 156 and the inferior endplate 154.

The superior spacer 188 has a pair of laterally spaced extensions 192,194 that extend distally from the main body 180 and configured to be disposed on opposite sides of the core 156 and lateral to the core. Each of the extensions 192,194 has a curved inner edge 196 which is designed to interface with the spherical shape 160 of the core 156 on its upper side 160.

The inferior spacer 190 also has a pair of laterally spaced extensions 198,200 that extend distally from the main body 180 and configured to be disposed on opposite sides of the core 156 on its underside and lateral to the core. Each of the extensions 198,200 has a straight inner side 201 such that the extensions run along the outer longitudinal edges of the rectangular shape 168 of the core 156 on its underside.

As shown in FIG. 33B, the superior spacer 188 has a higher thickness than the inferior spacer 190.

Figure 35:
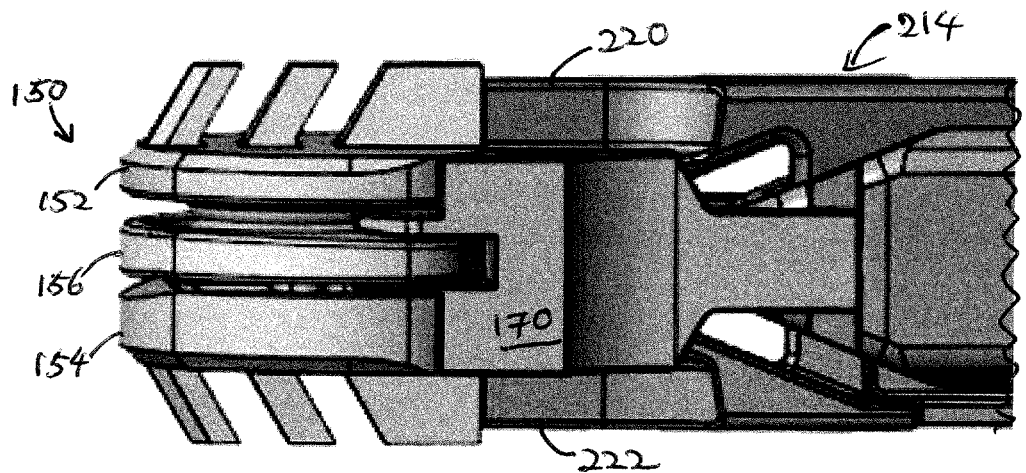
FIG. 35 is a side view of the cervical implant of FIG. 32 and an implant inserter securely attached to the implant and packaging insert according to another aspect of the present invention.
Figure 36:
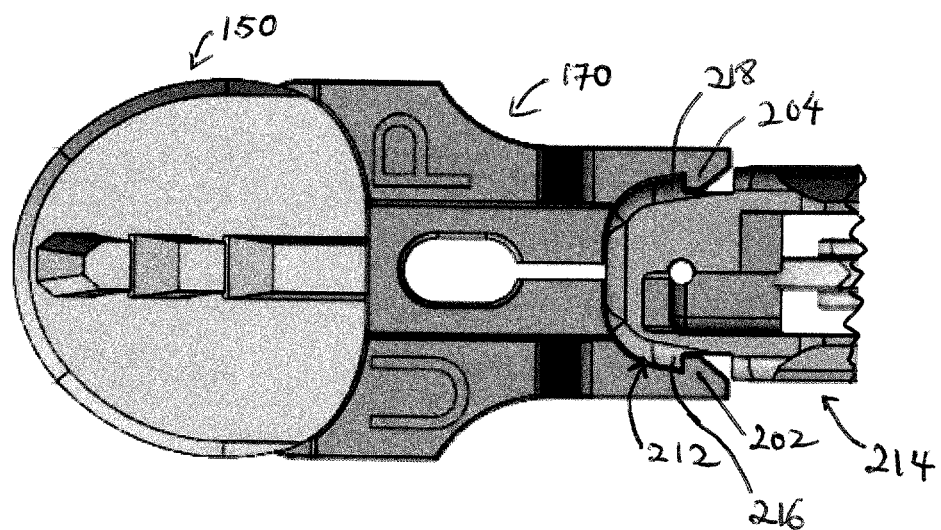
FIG. 36 is a plan view of the cervical implant of FIG. 32 and an implant inserter securely attached to the implant and packaging insert according to another aspect of the present invention. The arms of the implant holder are not shown for clarity.

The snap fit latch 184 includes a pair of legs 206,208 extending proximally from the main body 180 and a pair of hooks 202,204 disposed at a proximal end of the pair of legs. The pair of legs 206,208 are resiliently movable radially outwardly relative to the central axis 166 of the insert 170, and are adapted to snap fit over a pair of mating tabs 216,218 of the implant inserter 214. The proximal portions of the pair of legs 206,208 form a curved concave shape 210 complimentary to the convex shape 212 of a distal portion of the implant inserter 214 as shown in FIG. 35.

A pair of arms 220,222 of the implant inserter 214 are vertically spaced from each other and are designed to be inserted into the insertion opening 174,176 and moved toward each other to securely grab the implant 150.

Figure 37:
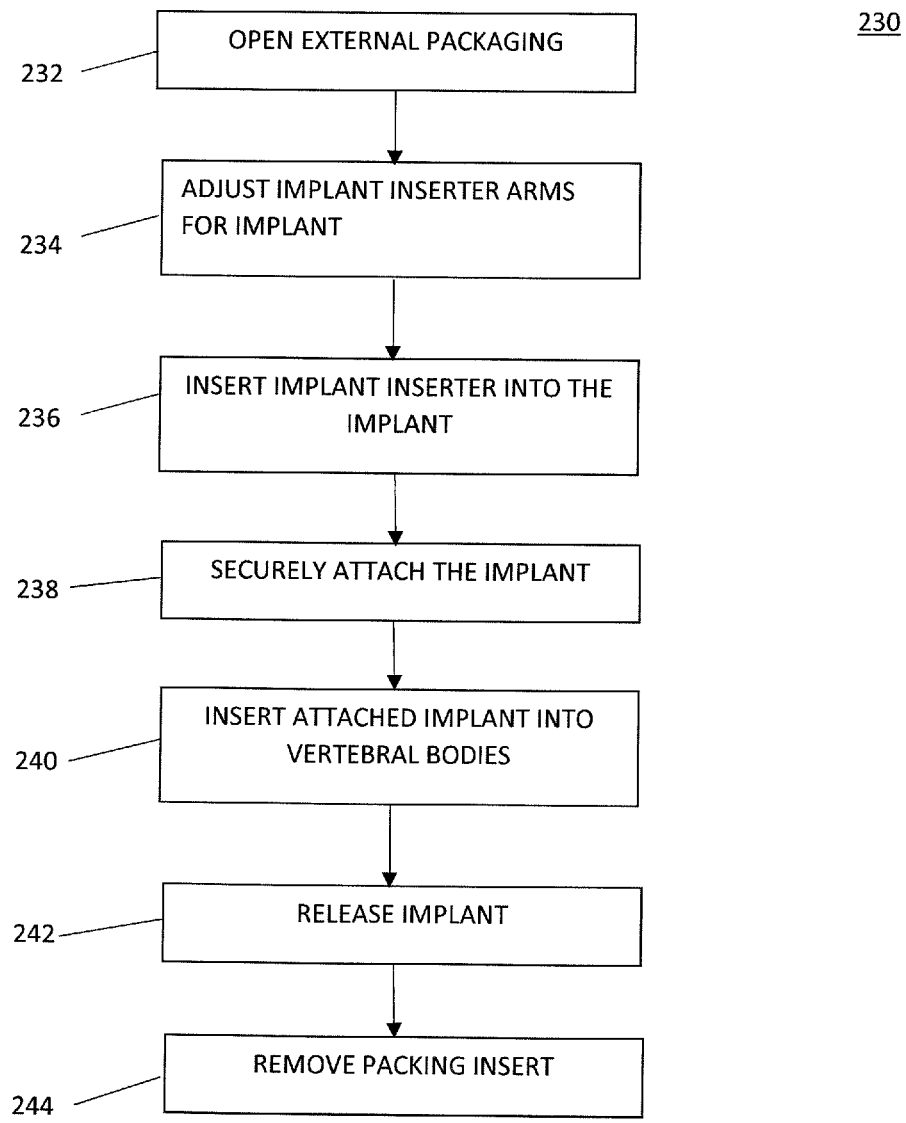
FIG. 37 is a flowchart of a method of placing an implant according to another aspect of the present invention.

A method of inserting an implant 150 with the packaging insert 170 will now be described with reference to FIG. 37. In step 232, an operator removes a cover (not shown) of the external packaging 172 to expose the implant 150 with the packaging insert 170. In step 234, the width of the arms 220,222 of the implant inserter 214 are adjusted to match the size of the implant 150 being used for the surgical procedure. In step 236, the tips of the arms 220,222 are inserted into the insertion opening 174,176 until the curved concave shape 210 of the packaging insert 170 is flush with the convex shape 212 of the implant inserter 214.

As the curved concave shape 210 of the packaging insert 170 moves closer towards the convex shape projection 212 of the implant inserter 214, the hooks 204 of the snap-fit latch 184 are resiliently moved laterally outwardly and snap fit over the pair of mating tabs 216,218 of the implant inserter 214 to securely lock the packaging insert 170 to the implant inserter.

In step 238, the arms 220, 222 of the implant inserter 214 are adjusted to reduce the width in order to securely attach the implant 150 and the packaging insert 170. As the arms 220,222 are tightening to bring them closer together, the presence of the spacer 186 prevents the endplates 152,154 from fish-mouthing (e.g., the distal ends of the endplates 152,154 widening relative to their proximal ends) and prevents the core 156 from translating prematurely.

In step 240, the implant 150 and packaging insert 170 attached to the implant inserter 214 are positioned and inserted into two adjacent vertebral bodies as a single unit. In step 242, once the implant 150 and packaging insert 170 are positioned in the vertebral bodies, the arms 220,222 are loosened to widen their width in order to release the implant 150 from the implant inserter 214. At this point, the packaging insert 170 is still securely attached to the implant inserter 214 due to the snap-fit latch 184.

In step 244, once the implant 150 has been released, the packaging insert 170 which is a disposable unit can be removed from the implant inserter 214 by, for example, twisting to release the lock and then disposed of or along the grooves until the insert has been released.

Figure 38:
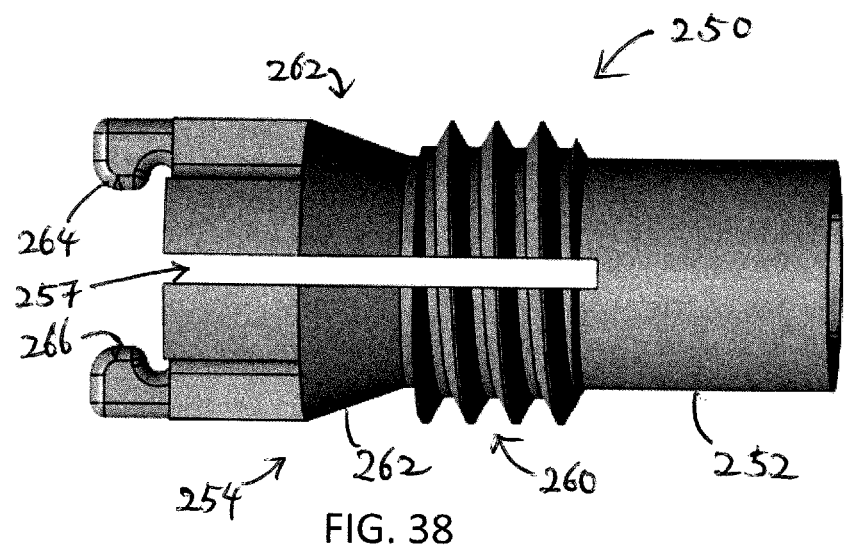
FIG. 38 is a perspective view of a packaging insert for the cervical implant of FIG. 32 according to another aspect of the present invention.

FIG. 38 illustrates an alternative embodiment of a packaging insert/cartridge 250 for the cervical implant of FIG. 32 according to another aspect of the present invention.

The packaging insert/cartridge 250 is also designed to be used with the implant 150. Similar to the implant 150 and packaging insert 170 as shown in FIG. 34, the implant 150 and cartridge 250 combination will be stored in a similar external packaging as that 172 shown in FIG. 34.

Figure 39:
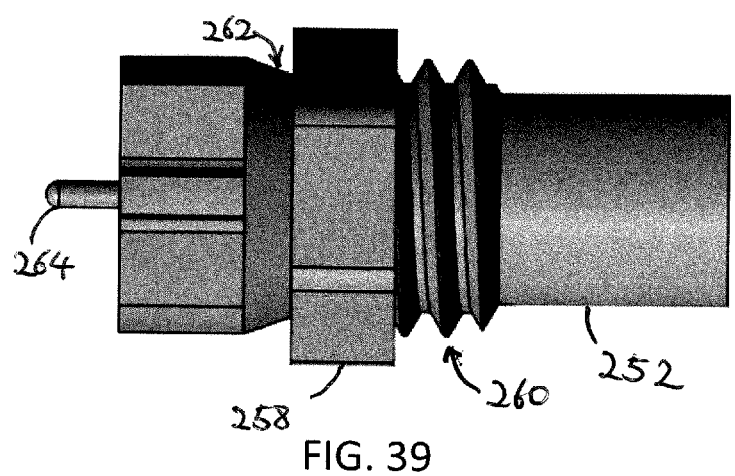
FIG. 39 is a plan view of the packaging insert of FIG. 38.
Figure 40:
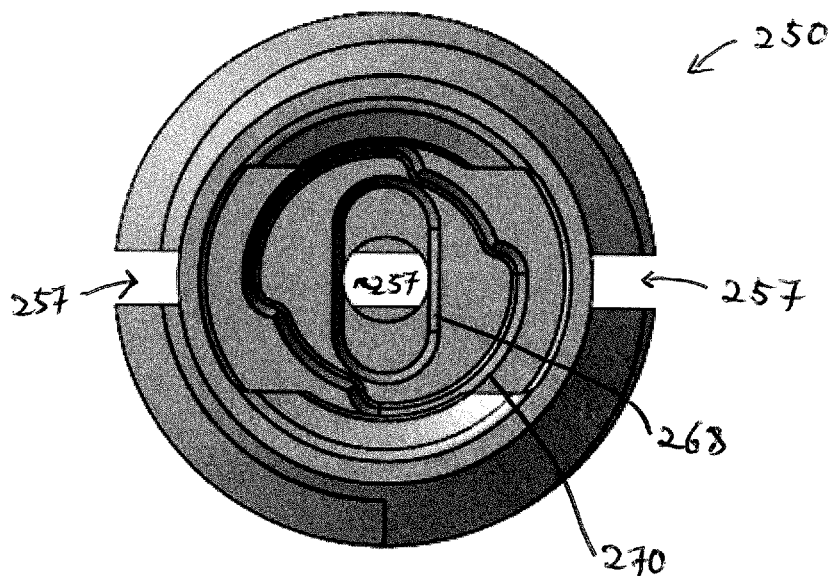
FIG. 40 is a rear view of the packaging insert of FIG. 38.

The cartridge 250 is designed to hold the implant 150 in a neutral orientation while it is being held by an insertion tool and inserted into the vertebral bodies. The packaging cartridge 250 includes a main body 252, first and second arms 254,256 extending distally from the main body and defining a gap 257, and a tightener such as a locking nut 258 (shown in FIG. 39). The arms 254,256 are spaced from each other and are configured to be resiliently flexed inwardly toward each other.

A proximal portion of each arm 254,256 has an externally threaded section 260, a conical section 262 extending distally from the threaded section 260, and a hook 264,266 at its distal portion. The pair of hooks 264,266 are circumferentially offset (e.g., 90 degrees) from the gap 257 and are designed to be inserted into the insertion openings 174,176 of the implant 150.

Figure 41:
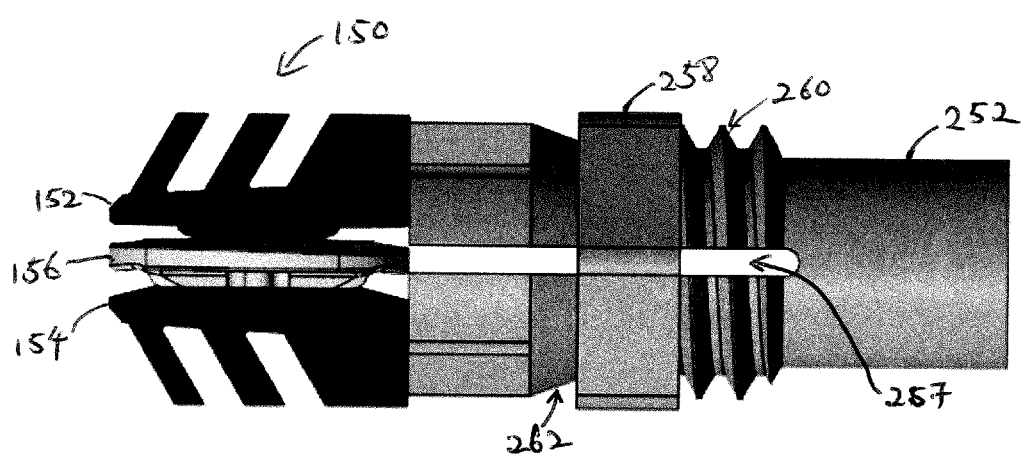
FIG. 41 is a side view of the implant of FIG. 32 and the packaging insert of FIG. 38.

The nut 258 has an internal threading and is threaded on the external threading 260 of the arms 254,256. As the nut 260 rotates and translates distally over the conical section 260,262 (see FIG. 39), the arms 254,256 and therefore the hooks 264,266 move toward each other in order to lock the cartridge 250 with the implant 150 as shown in FIG. 41.

The distal end of the cartridge 250 is designed to be attached to an implant inserter (not shown) for insertion into vertebral bodies. One exemplary inserter may be a quarter turn locking inserter which has an inner keyed tip inserted into a central keyed opening 268 and a keyed recess 270 disposed proximally of the central keyed opening 268.

A method of inserting the implant 150 with the packaging cartridge 250 into vertebral bodies is similar to that of inserting the implant 150 with the packaging insert 170. The cartridge 250 may come prepackaged with the implant 150 securely held in the external packaging with the locking nut 258 tightened. In that case, an implant inserter is brought to the cartridge 250 and is securely attached to the cartridge by using the quarter turn locking mechanism as discussed above. The attached cartridge with the implant 150 is then inserted into the vertebral bodies using the implant inserter. Once inserted, the locking nut 258 is rotated to translate it proximally while the cartridge 250 is still attached to the implant inserter. The proximal translation of the locking nut 258 widens the hooks 264,266 relative to each other to allow the cartridge to separate from the inserted implant 150. Once the cartridge 250 and the implant are separated, the cartridge can be removed from the implant inserter with a quarter turn and disposed of.

While it is apparent that the invention disclosed herein is well calculated to fulfill the objects stated above, it will be appreciated that numerous modifications and embodiments may be devised by those skilled in the art. While devices and methods are described in terms of "comprising," "containing," "having," or "including" various elements or steps, the devices and methods can also "consist essentially of" or "consist of" the various elements and steps.

What is claimed is:

1. A system having a packaging insert for use with an implant, comprising:
   the implant having first and second components; and
   the packaging insert comprising:
     a main body;
     a snap fit latch extending proximally from the main body, the snap fit latch adapted to snap fit over a mating part of an implant inserter;
     at least one spacer extending distally from the main body and configured to be disposed between the first and second components of the implant,
   wherein:
   the implant includes a core disposed between the first and second components, the core is adapted to move with respect to the first and second components; and
   the spacer includes:
     a superior spacer configured to be disposed between the core and the first component; and
     an inferior spacer configured to be disposed between the core and the second component.

2. The system of claim 1, wherein the superior spacer is thicker than the inferior spacer.

3. The system of claim 1, wherein the superior spacer includes first and second laterally spaced extensions configured to be disposed on opposite sides of the core.

4. The system of claim 1, wherein each of the superior and inferior spacers includes first and second laterally spaced extensions configured to be disposed on opposite sides of the core.

5. The system of claim 1, wherein the snap fit latch includes a pair of hooks adapted to snap fit over a pair of mating tabs of the implant inserter.

6. The system of claim 5, wherein the snap fit latch includes a pair of legs extending proximally from the main body and a pair of hooks disposed at a proximal end of the pair of legs, the pair of legs resiliently movable radially outwardly relative to a central axis of the main body.

7. The system of claim 6, wherein proximal portions of the pair of legs form a curved shape complimentary to the shape of a distal portion of the implant inserter.

8. A method for inserting an implant between adjacent vertebral bodies with a packaging insert and an implant inserter comprising:
   providing the implant, the implant having first and second components;
   providing the packaging insert, wherein the packaging insert comprises:
     a main body;
     a snap fit latch extending proximally from the main body, the snap fit latch including a pair of hooks adapted to snap fit over a mating part of an implant inserter; and
     at least one spacer extending distally from the main body and configured to be disposed between the first and second components of the implant to maintain a spacing between the first and second components,
wherein the packing insert is engaged with the implant such that the spacer is disposed between the first and second components;
providing the implant inserter, the implant inserter having a first arm and a second arm;
engaging the first arm with the first component, engaging the second arm with the second component and attaching the pair of hooks on the snap fit latch over the mating part of an implant inserter;
inserting the implant between adjacent vertebral bodies;
releasing the implant from the implant inserter; and
removing the packing insert from the implant.

9. The method of claim 8, wherein:
the implant includes a core disposed between the first and second components and adapted to pivot about the first and second components; and
the spacer includes:
  a superior spacer configured to be disposed between the core and the first component; and
  an inferior spacer configured to be disposed between the core and the second component.

10. The method of claim 8, wherein the engaging the first arm with the first component and engaging the second arm with the second component includes adjusting the distance between the arms to securely attach the implant to the implant inserter.

11. The method of claim 8, wherein packing insert is attached to the implant before the implant inserter is attached to the implant.

12. The method of claim 8, wherein releasing the implant inserter from the implant includes adjusting the distance between the arms to detach the implant to the implant inserter.

13. The method of claim 8, wherein the first arm engages with the only a rear potion of the first component the second arm engages with with a rear portion of the second component.

14. The method of claim 8, wherein a proximal portion of the snap fit latch between the pair of hooks forms a curved shape complimentary to the shape of a distal portion of the implant inserter.

* * * * *